US007863411B2

(12) United States Patent
Hammond et al.

(10) Patent No.: US 7,863,411 B2
(45) Date of Patent: Jan. 4, 2011

(54) PRION PROTEIN LIGANDS AND METHODS OF USE

(75) Inventors: David J. Hammond, Laytonsville, MD (US); Julia T. Lathrop, Falls Church, VA (US); Larisa Cervenakova, Rockville, MD (US); Ruben G. Carbonell, Raleigh, NC (US)

(73) Assignees: Pathogen Removal and Diagnostics Technologies Inc., Wilmington, DE (US); North Carolina State University, Raleigh, NC (US)

( * ) Notice: Subject to any disclaimer, the term of this patent is extended or adjusted under 35 U.S.C. 154(b) by 1395 days.

(21) Appl. No.: 10/727,335

(22) Filed: Dec. 3, 2003

(65) Prior Publication Data

US 2004/0229280 A1 Nov. 18, 2004

Related U.S. Application Data

(60) Provisional application No. 60/430,423, filed on Dec. 3, 2002.

(51) Int. Cl.
C07K 5/00 (2006.01)
(52) U.S. Cl. .................................... 530/300
(58) Field of Classification Search ........................ None
See application file for complete search history.

(56) References Cited

U.S. PATENT DOCUMENTS

| | | | |
|---|---|---|---|
| 4,849,408 A | 7/1989 | Sommermeyer et al. | |
| 5,010,175 A | 4/1991 | Rutter et al. | |
| 5,036,052 A | 7/1991 | Ozeki et al. | |
| 5,133,866 A | 7/1992 | Kauvar | |
| 5,281,539 A | 1/1994 | Schramm | |
| 5,312,730 A | 5/1994 | Piran et al. | |
| 5,498,538 A | 3/1996 | Kay et al. | |
| 5,525,492 A * | 6/1996 | Hill | 435/91.2 |
| 5,750,361 A * | 5/1998 | Prusiner et al. | 435/23 |
| 5,808,011 A | 9/1998 | Gawryl et al. | |
| 5,834,318 A | 11/1998 | Buettner et al. | |
| 5,888,834 A | 3/1999 | Ishikawa et al. | |
| 5,958,684 A | 9/1999 | Van Leeuwen et al. | |
| 6,126,939 A | 10/2000 | Eisenbach-Schwartz et al. | |
| 6,221,614 B1 | 4/2001 | Prusiner et al. | |
| 6,261,790 B1 * | 7/2001 | O'Rourke | 435/7.72 |
| 6,355,610 B2 * | 3/2002 | Chesebro et al. | 514/21.7 |
| 6,379,905 B1 | 4/2002 | Fishleigh et al. | |
| 6,437,102 B1 | 8/2002 | Lee et al. | |
| 6,451,541 B1 | 9/2002 | Winnacker et al. | |
| 6,582,965 B1 | 6/2003 | Townsend et al. | |
| 6,750,025 B1 | 6/2004 | Hammond et al. | |
| 6,995,141 B1 | 2/2006 | Sleath et al. | |
| 7,393,658 B2 | 7/2008 | Carbonell et al. | |
| 7,510,848 B2 | 3/2009 | Hammond et al. | |
| 2003/0092094 A1 | 5/2003 | Vey et al. | |
| 2004/0186273 A1 | 9/2004 | Hammond et al. | |

FOREIGN PATENT DOCUMENTS

| | | |
|---|---|---|
| WO | 91/13904 A1 | 9/1991 |
| WO | WO 92/00091 | 1/1992 |
| WO | WO01/71042 A2 * | 9/2001 |
| WO | WO 01/77687 | 10/2001 |
| WO | 01/81367 A2 | 11/2001 |
| WO | WO 03/016904 | 2/2003 |
| WO | 2006/102099 A2 | 9/2006 |

OTHER PUBLICATIONS

Hardt et al. J. Comp. Path. 2000, vol. 122, p. 43-53.*
Li et al. Biochemistry, 2000, vol. 39, p. 6296-6309.*
"International Search Report." Conducted for International Application No. PCT/US03/38343. Patent Cooperation Treaty: Nov. 17, 2004.
Schatzl, et al. "Prion Protein Gene Variation Among Primates." J. Mol. Biol. 1995, vol. 245, pp. 362-374.
Aubry et al., "N-Methyl Peptides. IV. Water and Beta-Turn in Peptides. Crystal Structure of N-Pivaloyl-L-Prolyl-N, N'-Dimethyl-D-Alaninamide in the Anhydrous and Monohydrated States", *Int. J. Pept. Protein Res.*, 18: 195-202 (1981).
Caughey, B., et al., "Binding of the Protease-Sensitive Form of Prion Protein PrP to Sulfated Glycosaminoglycan and Congo Red", *Journal of Virology*, 68: 2135-2141 (1994).
Degrado, W.F., "Design of Peptides and Proteins", *Adv. Protein Chem.*:39, 51-124, (1988).
Devlin, J.J. et al., "Random Peptide Libraries: A Source of Specific Protein Binding Molecules", *Science*: 249, 404-406 (1990).
Fischer, M.B. et al., "Binding of Disease-Associated Prion Protein to Plasminogen" ,*Nature*: 408, 479-483 (2000).
Furka, A. et al. "General Method for Rapid Synthesis of Multicomponent Peptide Mixtures", *Int. J. Peptide Protein Res.*:37, 487-493 (1991).
Ingrosso, L., et al., "Congo Red Prolongs the Incubation Period in Scrapie-Infected Hamsters", *Journal of Virology*: 69, 506-508 (1995).
Jameson, B.A. et al., "A Rationally Designed CD4 Analogue Inhibits Experimental Allergic Encephalomyelitis", *Nature*: 368, 744-746 (1994).
Kascsak, R.J., et al., "Immunodiagnosis of Prion Disease", *Immunological Invest.*: 26, 259-268 (1997).
Lam, K.S. et al., "A New Type of Synthetic Peptide Library for Identifying Ligand-Binding Activity", *Nature*: 354,82-84 (1991).

(Continued)

*Primary Examiner*—Zachariah Lucas
*Assistant Examiner*—Agnieszka Boesen
(74) *Attorney, Agent, or Firm*—Nixon Peabody LLP

(57) ABSTRACT

Ligands that bind to prion proteins and methods for using the ligands for detecting or removing a prion protein from a sample, such as a biological fluid or an environmental sample. The ligands are capable of binding to one or more forms of prion protein including cellular prion protein (PrPc), infectious prion protein (PrPsc), and recombinant prion protein (PrPr). Prions from various species, including humans and hamsters, are bound by the ligands. Also provided is a method of treating or retarding the development of a prion-associated pathology in a subject.

27 Claims, 6 Drawing Sheets

OTHER PUBLICATIONS

Soto et al., "Reversion Of Prion Protein Conformational Changes By Synthetic β-Sheet Breaker Peptides", *LANCET*: 355, 192-197 (2000).

Merrifield, B. "Solid Phase Synthesis", *Science*: 232, 341-3479 (1986).

Needleman, S.B. et al. "A General method Applicable to the Search for Similarities in the Amino Acid Sequence of Two Proteins", *J. Mol. Biol.*: 48, 443-453 (1970).

Pearson, W.R. et al. "Impoved Tools for Biological Sequence Comparison", *Proc. Natl. Acad. Sci. U.S.A.*:85, 2444-2448 (1988).

Priola, S.A., et al., "Porphyrin and Phthalocyanine Antiscrapie Compounds", *Science*: 287, 1503-1506 (2000).

Prusiner, S.B., "Molecular Biology of Prion Diseases", *Science*: 252, 1515-1522 (1991).

Rose et al. "Turns in Peptides And Proteins", *Molecular Biology of Prion Diseases Adv. Protein Chem.*: 37, 1-109 (1985).

Safar, J. et al., "Eight Prion Strains Have PrP(Sc) Molecules With Different Conformations", *Nature Medicine*: 4, 1157-1165 (1998).

Samson, W.K. et al. "A 35 Amino Acid Fragment of Leptin Inhibits Feeding in the Rat", *Endocrinology*: 137, 5182-5185 (1996).

Soto, C. et al., "Reversion of Prion Protein Conformational Changes in Synthetic Beta-Sheet Breaker Peptides", *Lancet*: 355, 192-197 (2000).

Stockell, et al., "Prion Protein Selectively Bindes Copper(II) Ions", *Biochemistry*: 37, 7185-7193 (1998).

Tagliavani, F., et al., "Effectiveness of Anthracycline Against Experimental Prion Diseases in Syrian Hamsters," *Science*: 276, 1119-1122 (1997).

Caspi et al., "The Anti-Prion Activity Of Congo Red", *J. Biol. Chem.*: 273, 3484-3489 (1999).

McHattle et al., "Clusterin Prevents Aggregation Of Neuropeptide 106-126 In Vitro", *Biochem. Biophys. Res. Commun*: 259, 336-340 (1999).

Chiarini et al., "Cellular Prion Protein Transduces Neuroprotective Signals," EMBO (European Molecular Biology Organization) Journal 21(13:3317-26 (2002).

Schmitt-Ulms et al., "Binding of Neural Cell Adhesion Molecules (N-CAMs) to the Cellular Prion Protein," J. Mol. Biol. 314:1209-25 (2001).

Windl et al., "A Candidate Marsupial PrP Gene Reveals Two Domains Conserved in mammalian Prp Proteins," Gene 159(181-6 (1995).

Search Report in corresponding EP application 03088431.

Kobayashi et al., "Relative Rates of Monoiodotyrosine and Diiodotyrosine Liberation During Enzymatic Hydrolysis of Iodinated Di- and Tripeptides," Endocrinology 92(6):1612-6 (1973).

GENESEQP Accession No. AAU49682 (Printed Aug. 9, 2009).

Uniport Accession No. P21734 (Printed Aug. 9, 2009).

Uniport Accession No. P90904 (Printed Aug. 9, 2009).

Uniport Accession No. Q7YX12 (Printed Aug. 9, 2009).

Uniport Accession No. Q8RHT9 (Printed Aug. 9, 2009).

Chen et al., "Fluorescense of Tryptophan Dipeptides: Correlations with the Rotamer Model," Biochemistry 30: 5184-5195 (1991).

Shimura et al., "Synthetic Oligopeptides as Isoelectric Point Markers for Capillary Isoelectric Focusing with Ultraviolet Absorption Detection," Electrophoresis 21: 603-610 (2000).

* cited by examiner

Bead Bound PrP

In PBS

1. MW
2. Control
3. Amine
4. HYD
5. RWD
6. SYA
7. SYF
8. YEY

In CPD

1. MW
2. Control
3. Amine
4. HYD
5. RWD
6. SYA
7. SYF
8. YEY

| LW | RWD | SYA | WEY | WSD |
|---|---|---|---|---|

| YID | YFE | YEY | WQD | |
|---|---|---|---|---|

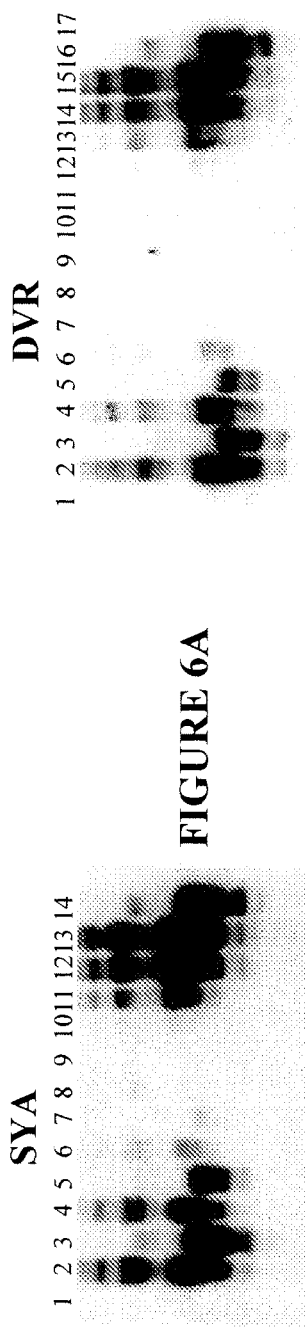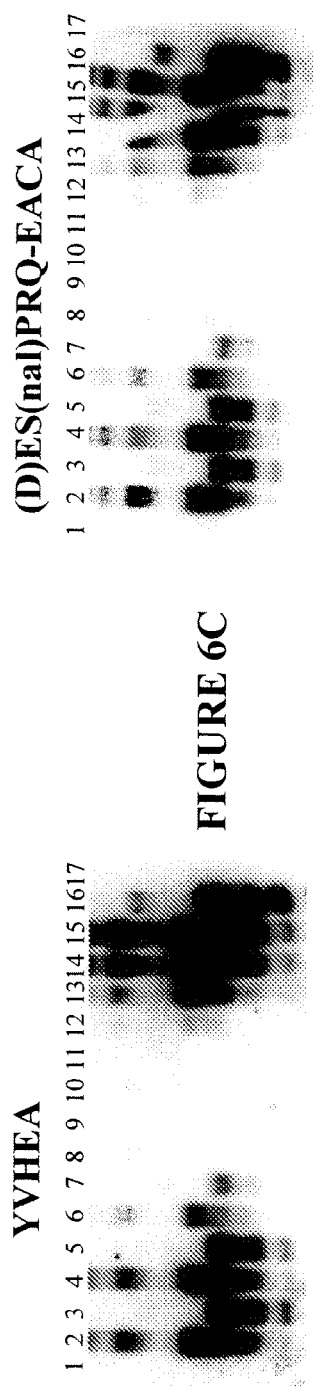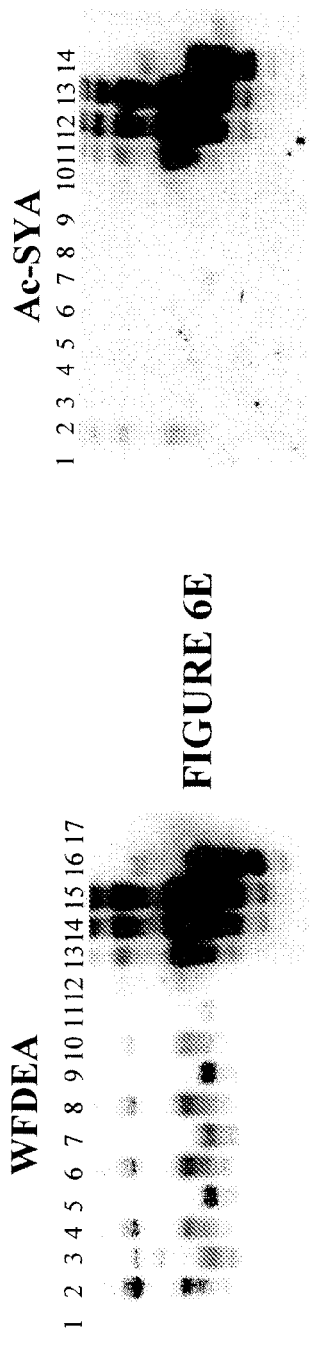

SEQUENCE LISTING

```
<160> NUMBER OF SEQ ID NOS: 226

<210> SEQ ID NO 1
<211> LENGTH: 5
<212> TYPE: PRT
<213> ORGANISM: prion sp.

<400> SEQUENCE: 1

Arg Tyr Pro Gly Gln
1               5

<210> SEQ ID NO 2
<211> LENGTH: 6
<212> TYPE: PRT
<213> ORGANISM: prion sp.

<400> SEQUENCE: 2

Asp Arg Tyr Tyr Arg Asp
1               5

<210> SEQ ID NO 3
```

```
<211> LENGTH: 6
<212> TYPE: PRT
<213> ORGANISM: prion sp.

<400> SEQUENCE: 3

Gln Ala Tyr Tyr Gln Arg
1               5

<210> SEQ ID NO 4
<211> LENGTH: 6
<212> TYPE: PRT
<213> ORGANISM: prion sp.

<400> SEQUENCE: 4

Gln Val Tyr Tyr Arg Pro
1               5

<210> SEQ ID NO 5
<211> LENGTH: 7
<212> TYPE: PRT
<213> ORGANISM: Artificial Sequence
<220> FEATURE:
<223> OTHER INFORMATION: prion-binding ligand

<400> SEQUENCE: 5

Lys Ile His Lys Phe Leu Ala
1               5

<210> SEQ ID NO 6
<211> LENGTH: 7
<212> TYPE: PRT
<213> ORGANISM: Artificial Sequence
<220> FEATURE:
<223> OTHER INFORMATION: prion-binding ligand

<400> SEQUENCE: 6

Gly Thr His Asp Phe Gln Ala
1               5

<210> SEQ ID NO 7
<211> LENGTH: 7
<212> TYPE: PRT
<213> ORGANISM: Artificial Sequence
<220> FEATURE:
<223> OTHER INFORMATION: prion-binding ligand

<400> SEQUENCE: 7

Lys Phe Gly Ser Thr His Ala
1               5

<210> SEQ ID NO 8
<211> LENGTH: 7
<212> TYPE: PRT
<213> ORGANISM: Artificial Sequence
<220> FEATURE:
<223> OTHER INFORMATION: prion-binding ligand

<400> SEQUENCE: 8

Phe Val Asn Glu Ile Glu Ala
1               5

<210> SEQ ID NO 9
<211> LENGTH: 7
<212> TYPE: PRT
<213> ORGANISM: Artificial Sequence
<220> FEATURE:
<223> OTHER INFORMATION: prion-binding ligand
```

```
<400> SEQUENCE: 9

Gly Leu His Phe Lys Ser Ala
1               5

<210> SEQ ID NO 10
<211> LENGTH: 7
<212> TYPE: PRT
<213> ORGANISM: Artificial Sequence
<220> FEATURE:
<223> OTHER INFORMATION: prion-binding ligand

<400> SEQUENCE: 10

Gly Arg Val Leu His His Ala
1               5

<210> SEQ ID NO 11
<211> LENGTH: 7
<212> TYPE: PRT
<213> ORGANISM: Artificial Sequence
<220> FEATURE:
<223> OTHER INFORMATION: prion-binding ligand

<400> SEQUENCE: 11

Gln Lys Asn Ser Glu Trp Ala
1               5

<210> SEQ ID NO 12
<211> LENGTH: 7
<212> TYPE: PRT
<213> ORGANISM: Artificial Sequence
<220> FEATURE:
<223> OTHER INFORMATION: prion-binding ligand

<400> SEQUENCE: 12

His Ala Tyr Phe Thr His Ala
1               5

<210> SEQ ID NO 13
<211> LENGTH: 7
<212> TYPE: PRT
<213> ORGANISM: Artificial Sequence
<220> FEATURE:
<223> OTHER INFORMATION: prion-binding ligand

<400> SEQUENCE: 13

Trp Pro Lys Gly Ala Val Ala
1               5

<210> SEQ ID NO 14
<211> LENGTH: 7
<212> TYPE: PRT
<213> ORGANISM: Artificial Sequence
<220> FEATURE:
<223> OTHER INFORMATION: prion-binding ligand

<400> SEQUENCE: 14

Arg Pro Trp Lys Lys Ala Ala
1               5

<210> SEQ ID NO 15
<211> LENGTH: 7
<212> TYPE: PRT
<213> ORGANISM: Artificial Sequence
<220> FEATURE:
<223> OTHER INFORMATION: prion-binding ligand
```

```
<400> SEQUENCE: 15

Pro Lys His Ile Trp Pro Ala
1               5

<210> SEQ ID NO 16
<211> LENGTH: 7
<212> TYPE: PRT
<213> ORGANISM: Artificial Sequence
<220> FEATURE:
<223> OTHER INFORMATION: prion-binding ligand

<400> SEQUENCE: 16

His Lys Leu Trp Gly Val Ala
1               5

<210> SEQ ID NO 17
<211> LENGTH: 7
<212> TYPE: PRT
<213> ORGANISM: Artificial Sequence
<220> FEATURE:
<223> OTHER INFORMATION: prion-binding ligand

<400> SEQUENCE: 17

Gly Gly Tyr Lys Pro Tyr Ala
1               5

<210> SEQ ID NO 18
<211> LENGTH: 7
<212> TYPE: PRT
<213> ORGANISM: Artificial Sequence
<220> FEATURE:
<223> OTHER INFORMATION: prion-binding ligand

<400> SEQUENCE: 18

Glu Asn Val Ser Gln Asn Ala
1               5

<210> SEQ ID NO 19
<211> LENGTH: 7
<212> TYPE: PRT
<213> ORGANISM: Artificial Sequence
<220> FEATURE:
<223> OTHER INFORMATION: prion-binding ligand

<400> SEQUENCE: 19

His Thr Tyr Tyr Asn Gly Ala
1               5

<210> SEQ ID NO 20
<211> LENGTH: 7
<212> TYPE: PRT
<213> ORGANISM: Artificial Sequence
<220> FEATURE:
<223> OTHER INFORMATION: prion-binding ligand

<400> SEQUENCE: 20

Lys Lys Lys Ser Asp His Ala
1               5

<210> SEQ ID NO 21
<211> LENGTH: 7
<212> TYPE: PRT
<213> ORGANISM: Artificial Sequence
<220> FEATURE:
<223> OTHER INFORMATION: prion-binding ligand

<400> SEQUENCE: 21
```

His His Leu Lys Gly Thr Ala
1               5

<210> SEQ ID NO 22
<211> LENGTH: 7
<212> TYPE: PRT
<213> ORGANISM: Artificial Sequence
<220> FEATURE:
<223> OTHER INFORMATION: prion-binding ligand

<400> SEQUENCE: 22

Lys Lys His Gly Val Trp Ala
1               5

<210> SEQ ID NO 23
<211> LENGTH: 7
<212> TYPE: PRT
<213> ORGANISM: Artificial Sequence
<220> FEATURE:
<223> OTHER INFORMATION: prion-binding ligand

<400> SEQUENCE: 23

Asp Gly Thr Gln Ala His Ala
1               5

<210> SEQ ID NO 24
<211> LENGTH: 7
<212> TYPE: PRT
<213> ORGANISM: Artificial Sequence
<220> FEATURE:
<223> OTHER INFORMATION: prion-binding ligand

<400> SEQUENCE: 24

Ala Pro His Arg Asn Asn Ala
1               5

<210> SEQ ID NO 25
<211> LENGTH: 7
<212> TYPE: PRT
<213> ORGANISM: Artificial Sequence
<220> FEATURE:
<223> OTHER INFORMATION: prion-binding ligand

<400> SEQUENCE: 25

His His Gly His Asn Ile Ala
1               5

<210> SEQ ID NO 26
<211> LENGTH: 7
<212> TYPE: PRT
<213> ORGANISM: Artificial Sequence
<220> FEATURE:
<223> OTHER INFORMATION: prion-binding ligand

<400> SEQUENCE: 26

His Thr Trp His Gly Gln Ala
1               5

<210> SEQ ID NO 27
<211> LENGTH: 7
<212> TYPE: PRT
<213> ORGANISM: Artificial Sequence
<220> FEATURE:
<223> OTHER INFORMATION: prion-binding ligand

<400> SEQUENCE: 27

His Val Phe Val Thr Trp Ala
1               5

<210> SEQ ID NO 28
<211> LENGTH: 7
<212> TYPE: PRT
<213> ORGANISM: Artificial Sequence
<220> FEATURE:
<223> OTHER INFORMATION: prion-binding ligand

<400> SEQUENCE: 28

Thr His His Phe Tyr Ile Ala
1               5

<210> SEQ ID NO 29
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (6)..(6)
<223> OTHER INFORMATION: Xaa at position 6 = Ala or Gly

<400> SEQUENCE: 29

Lys Leu Gly Trp Gly Xaa Ala
1               5

<210> SEQ ID NO 30
<211> LENGTH: 7
<212> TYPE: PRT
<213> ORGANISM: Artificial Sequence
<220> FEATURE:
<223> OTHER INFORMATION: prion-binding ligand

<400> SEQUENCE: 30

Gly Ser Lys Lys Lys Glu Ala
1               5

<210> SEQ ID NO 31
<211> LENGTH: 7
<212> TYPE: PRT
<213> ORGANISM: Artificial Sequence
<220> FEATURE:
<223> OTHER INFORMATION: prion-binding ligand

<400> SEQUENCE: 31

Pro Leu Leu Val Val Trp Ala
1               5

<210> SEQ ID NO 32
<211> LENGTH: 7
<212> TYPE: PRT
<213> ORGANISM: Artificial Sequence
<220> FEATURE:
<223> OTHER INFORMATION: prion-binding ligand

<400> SEQUENCE: 32

Trp Leu Leu Val Gly Gly Ala
1               5

<210> SEQ ID NO 33
<211> LENGTH: 7
<212> TYPE: PRT
<213> ORGANISM: Artificial Sequence
<220> FEATURE:
<223> OTHER INFORMATION: prion-binding ligand

```
<220> FEATURE:
<221> NAME/KEY: MISC_FEATURE
<222> LOCATION: (1)..(1)
<223> OTHER INFORMATION: Xaa at position 1 = Trp or Gly

<400> SEQUENCE: 33

Xaa Gln Val Leu Val Tyr Ala
1               5

<210> SEQ ID NO 34
<211> LENGTH: 7
<212> TYPE: PRT
<213> ORGANISM: Artificial Sequence
<220> FEATURE:
<223> OTHER INFORMATION: prion-binding ligand

<400> SEQUENCE: 34

Arg Arg His Gln Arg Gln Ala
1               5

<210> SEQ ID NO 35
<211> LENGTH: 7
<212> TYPE: PRT
<213> ORGANISM: Artificial Sequence
<220> FEATURE:
<223> OTHER INFORMATION: prion-binding ligand

<400> SEQUENCE: 35

Leu Pro Trp Thr Phe Gly Ala
1               5

<210> SEQ ID NO 36
<211> LENGTH: 7
<212> TYPE: PRT
<213> ORGANISM: Artificial Sequence
<220> FEATURE:
<223> OTHER INFORMATION: prion-binding ligand

<400> SEQUENCE: 36

Ile Phe Ile Ile Ile Thr Ala
1               5

<210> SEQ ID NO 37
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (2)..(2)
<223> OTHER INFORMATION: Xaa at position 2 is unknown

<400> SEQUENCE: 37

Pro Xaa Ile Glu Pro His Ala
1               5

<210> SEQ ID NO 38
<211> LENGTH: 7
<212> TYPE: PRT
<213> ORGANISM: Artificial Sequence
<220> FEATURE:
<223> OTHER INFORMATION: prion-binding ligand

<400> SEQUENCE: 38

Glu Trp Gly Ile Ile Trp Ala
1               5
```

```
<210> SEQ ID NO 39
<211> LENGTH: 7
<212> TYPE: PRT
<213> ORGANISM: Artificial Sequence
<220> FEATURE:
<223> OTHER INFORMATION: prion-binding ligand

<400> SEQUENCE: 39

Gly Trp Tyr Ile Tyr Phe Ala
1               5

<210> SEQ ID NO 40
<211> LENGTH: 7
<212> TYPE: PRT
<213> ORGANISM: Artificial Sequence
<220> FEATURE:
<223> OTHER INFORMATION: prion-binding ligand

<400> SEQUENCE: 40

Thr Leu Ile Leu Phe His Ala
1               5

<210> SEQ ID NO 41
<211> LENGTH: 7
<212> TYPE: PRT
<213> ORGANISM: Artificial Sequence
<220> FEATURE:
<223> OTHER INFORMATION: prion-binding ligand

<400> SEQUENCE: 41

Phe Leu Leu Ser Asn His Ala
1               5

<210> SEQ ID NO 42
<211> LENGTH: 7
<212> TYPE: PRT
<213> ORGANISM: Artificial Sequence
<220> FEATURE:
<223> OTHER INFORMATION: prion-binding ligand

<400> SEQUENCE: 42

Trp Gln Ile Arg Phe Phe Ala
1               5

<210> SEQ ID NO 43
<211> LENGTH: 7
<212> TYPE: PRT
<213> ORGANISM: Artificial Sequence
<220> FEATURE:
<223> OTHER INFORMATION: prion-binding ligand

<400> SEQUENCE: 43

Val Leu Leu Val Phe Glu Ala
1               5

<210> SEQ ID NO 44
<211> LENGTH: 7
<212> TYPE: PRT
<213> ORGANISM: Artificial Sequence
<220> FEATURE:
<223> OTHER INFORMATION: prion-binding ligand

<400> SEQUENCE: 44

Gly Trp Val Leu Glu Ile Ala
1               5
```

```
<210> SEQ ID NO 45
<211> LENGTH: 7
<212> TYPE: PRT
<213> ORGANISM: Artificial Sequence
<220> FEATURE:
<223> OTHER INFORMATION: prion-binding ligand

<400> SEQUENCE: 45

Phe Leu Leu Ile Asp Thr Ala
1               5

<210> SEQ ID NO 46
<211> LENGTH: 7
<212> TYPE: PRT
<213> ORGANISM: Artificial Sequence
<220> FEATURE:
<223> OTHER INFORMATION: prion-binding ligand

<400> SEQUENCE: 46

Gly Phe Leu Phe Lys Phe Ala
1               5

<210> SEQ ID NO 47
<211> LENGTH: 7
<212> TYPE: PRT
<213> ORGANISM: Artificial Sequence
<220> FEATURE:
<223> OTHER INFORMATION: prion-binding ligand

<400> SEQUENCE: 47

Pro Trp Thr Ile Tyr Ile Ala
1               5

<210> SEQ ID NO 48
<211> LENGTH: 2
<212> TYPE: PRT
<213> ORGANISM: Artificial Sequence
<220> FEATURE:
<223> OTHER INFORMATION: prion-binding ligand

<400> SEQUENCE: 48

Trp His
1

<210> SEQ ID NO 49
<211> LENGTH: 2
<212> TYPE: PRT
<213> ORGANISM: Artificial Sequence
<220> FEATURE:
<223> OTHER INFORMATION: prion-binding ligand

<400> SEQUENCE: 49

Trp Trp
1

<210> SEQ ID NO 50
<211> LENGTH: 2
<212> TYPE: PRT
<213> ORGANISM: Artificial Sequence
<220> FEATURE:
<223> OTHER INFORMATION: prion-binding ligand

<400> SEQUENCE: 50

Leu Trp
1

<210> SEQ ID NO 51
```

```
<211> LENGTH: 3
<212> TYPE: PRT
<213> ORGANISM: Artificial Sequence
<220> FEATURE:
<223> OTHER INFORMATION: prion-binding ligand

<400> SEQUENCE: 51

Trp Asn Ala
1

<210> SEQ ID NO 52
<211> LENGTH: 3
<212> TYPE: PRT
<213> ORGANISM: Artificial Sequence
<220> FEATURE:
<223> OTHER INFORMATION: prion-binding ligand

<400> SEQUENCE: 52

Glu Phe Trp
1

<210> SEQ ID NO 53
<211> LENGTH: 3
<212> TYPE: PRT
<213> ORGANISM: Artificial Sequence
<220> FEATURE:
<223> OTHER INFORMATION: prion-binding ligand

<400> SEQUENCE: 53

Leu Pro Trp
1

<210> SEQ ID NO 54
<211> LENGTH: 3
<212> TYPE: PRT
<213> ORGANISM: Artificial Sequence
<220> FEATURE:
<223> OTHER INFORMATION: prion-binding ligand

<400> SEQUENCE: 54

Tyr Glu Tyr
1

<210> SEQ ID NO 55
<211> LENGTH: 3
<212> TYPE: PRT
<213> ORGANISM: Artificial Sequence
<220> FEATURE:
<223> OTHER INFORMATION: prion-binding ligand

<400> SEQUENCE: 55

Trp Pro Ala
1

<210> SEQ ID NO 56
<211> LENGTH: 3
<212> TYPE: PRT
<213> ORGANISM: Artificial Sequence
<220> FEATURE:
<223> OTHER INFORMATION: prion-binding ligand

<400> SEQUENCE: 56

Phe Asn Gln
1

<210> SEQ ID NO 57
<211> LENGTH: 3
```

```
<212> TYPE: PRT
<213> ORGANISM: Artificial Sequence
<220> FEATURE:
<223> OTHER INFORMATION: prion-binding ligand

<400> SEQUENCE: 57

Tyr His Glu
1

<210> SEQ ID NO 58
<211> LENGTH: 3
<212> TYPE: PRT
<213> ORGANISM: Artificial Sequence
<220> FEATURE:
<223> OTHER INFORMATION: prion-binding ligand

<400> SEQUENCE: 58

Leu Phe Ala
1

<210> SEQ ID NO 59
<211> LENGTH: 3
<212> TYPE: PRT
<213> ORGANISM: Artificial Sequence
<220> FEATURE:
<223> OTHER INFORMATION: prion-binding ligand

<400> SEQUENCE: 59

Asn His Tyr
1

<210> SEQ ID NO 60
<211> LENGTH: 3
<212> TYPE: PRT
<213> ORGANISM: Artificial Sequence
<220> FEATURE:
<223> OTHER INFORMATION: prion-binding ligand

<400> SEQUENCE: 60

Thr Leu Gly
1

<210> SEQ ID NO 61
<211> LENGTH: 3
<212> TYPE: PRT
<213> ORGANISM: Artificial Sequence
<220> FEATURE:
<223> OTHER INFORMATION: prion-binding ligand

<400> SEQUENCE: 61

Trp Val Asp
1

<210> SEQ ID NO 62
<211> LENGTH: 5
<212> TYPE: PRT
<213> ORGANISM: Artificial Sequence
<220> FEATURE:
<223> OTHER INFORMATION: prion-binding ligand

<400> SEQUENCE: 62

Tyr Trp Asp Gln Ala
1               5

<210> SEQ ID NO 63
<211> LENGTH: 5
<212> TYPE: PRT
```

```
<213> ORGANISM: Artificial Sequence
<220> FEATURE:
<223> OTHER INFORMATION: prion-binding ligand

<400> SEQUENCE: 63

Tyr Val His Glu Ala
1               5

<210> SEQ ID NO 64
<211> LENGTH: 5
<212> TYPE: PRT
<213> ORGANISM: Artificial Sequence
<220> FEATURE:
<223> OTHER INFORMATION: prion-binding ligand

<400> SEQUENCE: 64

Trp Phe Asp Glu Ala
1               5

<210> SEQ ID NO 65
<211> LENGTH: 6
<212> TYPE: PRT
<213> ORGANISM: Artificial Sequence
<220> FEATURE:
<223> OTHER INFORMATION: prion-binding ligand

<400> SEQUENCE: 65

Leu Gln Trp Tyr Asp Ala
1               5

<210> SEQ ID NO 66
<211> LENGTH: 6
<212> TYPE: PRT
<213> ORGANISM: Artificial Sequence
<220> FEATURE:
<223> OTHER INFORMATION: prion-binding ligand

<400> SEQUENCE: 66

Tyr Thr His Ser Glu Ala
1               5

<210> SEQ ID NO 67
<211> LENGTH: 6
<212> TYPE: PRT
<213> ORGANISM: Artificial Sequence
<220> FEATURE:
<223> OTHER INFORMATION: prion-binding ligand

<400> SEQUENCE: 67

Trp Ile Asp Tyr Glu Ala
1               5

<210> SEQ ID NO 68
<211> LENGTH: 6
<212> TYPE: PRT
<213> ORGANISM: Artificial Sequence
<220> FEATURE:
<223> OTHER INFORMATION: prion-binding ligand

<400> SEQUENCE: 68

Val Trp Ile Asp Ala Ala
1               5

<210> SEQ ID NO 69
<211> LENGTH: 7
<212> TYPE: PRT
<213> ORGANISM: Artificial Sequence
```

```
<220> FEATURE:
<223> OTHER INFORMATION: prion-binding ligand

<400> SEQUENCE: 69

Trp Asp Glu Ala Glu Glu Ala
1               5

<210> SEQ ID NO 70
<211> LENGTH: 7
<212> TYPE: PRT
<213> ORGANISM: Artificial Sequence
<220> FEATURE:
<223> OTHER INFORMATION: prion-binding ligand

<400> SEQUENCE: 70

Tyr Asp Ser Tyr Asp Asp Ala
1               5

<210> SEQ ID NO 71
<211> LENGTH: 7
<212> TYPE: PRT
<213> ORGANISM: Artificial Sequence
<220> FEATURE:
<223> OTHER INFORMATION: prion-binding ligand

<400> SEQUENCE: 71

Asn Asp Phe Ile Asp Phe Ala
1               5

<210> SEQ ID NO 72
<211> LENGTH: 7
<212> TYPE: PRT
<213> ORGANISM: Artificial Sequence
<220> FEATURE:
<223> OTHER INFORMATION: prion-binding ligand

<400> SEQUENCE: 72

Tyr Glu Pro Trp Gly Ser Ala
1               5

<210> SEQ ID NO 73
<211> LENGTH: 7
<212> TYPE: PRT
<213> ORGANISM: Artificial Sequence
<220> FEATURE:
<223> OTHER INFORMATION: prion-binding ligand

<400> SEQUENCE: 73

Glu Tyr Gly Asp Trp Trp Ala
1               5

<210> SEQ ID NO 74
<211> LENGTH: 7
<212> TYPE: PRT
<213> ORGANISM: Artificial Sequence
<220> FEATURE:
<223> OTHER INFORMATION: prion-binding ligand

<400> SEQUENCE: 74

Trp Asp Tyr Asp Gln Glu Ala
1               5

<210> SEQ ID NO 75
<211> LENGTH: 7
<212> TYPE: PRT
<213> ORGANISM: Artificial Sequence
<220> FEATURE:
```

-continued

<223> OTHER INFORMATION: prion-binding ligand

<400> SEQUENCE: 75

Asp Trp Gly Asp Pro Phe Ala
1               5

<210> SEQ ID NO 76
<211> LENGTH: 7
<212> TYPE: PRT
<213> ORGANISM: Artificial Sequence
<220> FEATURE:
<223> OTHER INFORMATION: prion-binding ligand

<400> SEQUENCE: 76

Asp Trp Pro Glu Val Trp Ala
1               5

<210> SEQ ID NO 77
<211> LENGTH: 7
<212> TYPE: PRT
<213> ORGANISM: Artificial Sequence
<220> FEATURE:
<223> OTHER INFORMATION: prion-binding ligand

<400> SEQUENCE: 77

Phe His Asp Phe Ser Glu Ala
1               5

<210> SEQ ID NO 78
<211> LENGTH: 7
<212> TYPE: PRT
<213> ORGANISM: Artificial Sequence
<220> FEATURE:
<223> OTHER INFORMATION: prion-binding ligand

<400> SEQUENCE: 78

Asp Thr Phe Trp Asp Tyr Ala
1               5

<210> SEQ ID NO 79
<211> LENGTH: 7
<212> TYPE: PRT
<213> ORGANISM: Artificial Sequence
<220> FEATURE:
<223> OTHER INFORMATION: prion-binding ligand

<400> SEQUENCE: 79

Trp Asn Asp Leu Asp Asn Ala
1               5

<210> SEQ ID NO 80
<211> LENGTH: 7
<212> TYPE: PRT
<213> ORGANISM: Artificial Sequence
<220> FEATURE:
<223> OTHER INFORMATION: prion-binding ligand

<400> SEQUENCE: 80

Ala Ser Ala Leu Val Tyr Ala
1               5

<210> SEQ ID NO 81
<211> LENGTH: 7
<212> TYPE: PRT
<213> ORGANISM: Artificial Sequence
<220> FEATURE:
<223> OTHER INFORMATION: prion-binding ligand

```
<400> SEQUENCE: 81

Leu Ile Asn Ala Gly Gly Ala
1               5

<210> SEQ ID NO 82
<211> LENGTH: 7
<212> TYPE: PRT
<213> ORGANISM: Artificial Sequence
<220> FEATURE:
<223> OTHER INFORMATION: prion-binding ligand

<400> SEQUENCE: 82

Trp Glu Ser Tyr Val Thr Ala
1               5

<210> SEQ ID NO 83
<211> LENGTH: 7
<212> TYPE: PRT
<213> ORGANISM: Artificial Sequence
<220> FEATURE:
<223> OTHER INFORMATION: prion-binding ligand

<400> SEQUENCE: 83

Trp Ser Asp Glu Gly Tyr Ala
1               5

<210> SEQ ID NO 84
<211> LENGTH: 7
<212> TYPE: PRT
<213> ORGANISM: Artificial Sequence
<220> FEATURE:
<223> OTHER INFORMATION: prion-binding ligand

<400> SEQUENCE: 84

Tyr Arg Trp Thr Gly Pro Ala
1               5

<210> SEQ ID NO 85
<211> LENGTH: 7
<212> TYPE: PRT
<213> ORGANISM: Artificial Sequence
<220> FEATURE:
<223> OTHER INFORMATION: prion-binding ligand

<400> SEQUENCE: 85

Tyr Glu Asp Gln Trp Gln Ala
1               5

<210> SEQ ID NO 86
<211> LENGTH: 7
<212> TYPE: PRT
<213> ORGANISM: Artificial Sequence
<220> FEATURE:
<223> OTHER INFORMATION: prion-binding ligand

<400> SEQUENCE: 86

Glu Trp Ala Asp Asp Asn Ala
1               5

<210> SEQ ID NO 87
<211> LENGTH: 7
<212> TYPE: PRT
<213> ORGANISM: Artificial Sequence
<220> FEATURE:
<223> OTHER INFORMATION: prion-binding ligand
```

```
<400> SEQUENCE: 87

Tyr Glu Ile Asp Tyr Gly Ala
1               5

<210> SEQ ID NO 88
<211> LENGTH: 7
<212> TYPE: PRT
<213> ORGANISM: Artificial Sequence
<220> FEATURE:
<223> OTHER INFORMATION: prion-binding ligand

<400> SEQUENCE: 88

Glu Phe Gly Tyr Phe Asp Ala
1               5

<210> SEQ ID NO 89
<211> LENGTH: 7
<212> TYPE: PRT
<213> ORGANISM: Artificial Sequence
<220> FEATURE:
<223> OTHER INFORMATION: prion-binding ligand

<400> SEQUENCE: 89

Trp Gly Asp Glu Gln Asp Ala
1               5

<210> SEQ ID NO 90
<211> LENGTH: 7
<212> TYPE: PRT
<213> ORGANISM: Artificial Sequence
<220> FEATURE:
<223> OTHER INFORMATION: prion-binding ligand

<400> SEQUENCE: 90

His Glu Glu Asp Trp Ala Ala
1               5

<210> SEQ ID NO 91
<211> LENGTH: 7
<212> TYPE: PRT
<213> ORGANISM: Artificial Sequence
<220> FEATURE:
<223> OTHER INFORMATION: prion-binding ligand

<400> SEQUENCE: 91

Phe Glu Asp Phe Glu Leu Ala
1               5

<210> SEQ ID NO 92
<211> LENGTH: 7
<212> TYPE: PRT
<213> ORGANISM: Artificial Sequence
<220> FEATURE:
<223> OTHER INFORMATION: prion-binding ligand

<400> SEQUENCE: 92

Thr Trp Gly Ile Asp Glu Ala
1               5

<210> SEQ ID NO 93
<211> LENGTH: 7
<212> TYPE: PRT
<213> ORGANISM: Artificial Sequence
<220> FEATURE:
<223> OTHER INFORMATION: prion-binding ligand

<400> SEQUENCE: 93
```

```
Trp Asp Pro Thr Asp Tyr Ala
1               5
```

<210> SEQ ID NO 94
<211> LENGTH: 7
<212> TYPE: PRT
<213> ORGANISM: Artificial Sequence
<220> FEATURE:
<223> OTHER INFORMATION: prion-binding ligand

<400> SEQUENCE: 94

```
Asn Asp Lys Ile His Thr Ala
1               5
```

<210> SEQ ID NO 95
<211> LENGTH: 7
<212> TYPE: PRT
<213> ORGANISM: Artificial Sequence
<220> FEATURE:
<223> OTHER INFORMATION: prion-binding ligand

<400> SEQUENCE: 95

```
Phe Glu Asp Phe Phe Ser Ala
1               5
```

<210> SEQ ID NO 96
<211> LENGTH: 7
<212> TYPE: PRT
<213> ORGANISM: Artificial Sequence
<220> FEATURE:
<223> OTHER INFORMATION: prion-binding ligand

<400> SEQUENCE: 96

```
Tyr Glu Trp Ala Glu Gln Ala
1               5
```

<210> SEQ ID NO 97
<211> LENGTH: 7
<212> TYPE: PRT
<213> ORGANISM: Artificial Sequence
<220> FEATURE:
<223> OTHER INFORMATION: prion-binding ligand

<400> SEQUENCE: 97

```
Thr His Val Tyr Phe Leu Ala
1               5
```

<210> SEQ ID NO 98
<211> LENGTH: 6
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (1)..(1)
<223> OTHER INFORMATION: Xaa at position 1 is Ser, Thr or Trp

<400> SEQUENCE: 98

```
Xaa Asp Phe Ser Asp Ala
1               5
```

<210> SEQ ID NO 99
<211> LENGTH: 7
<212> TYPE: PRT
<213> ORGANISM: Artificial Sequence
<220> FEATURE:

<223> OTHER INFORMATION: prion-binding ligand

<400> SEQUENCE: 99

Tyr Arg Thr Pro Asn Glu Ala
1               5

<210> SEQ ID NO 100
<211> LENGTH: 6
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (1)..(1)
<223> OTHER INFORMATION: Xaa at position 1 is either Gly or Leu

<400> SEQUENCE: 100

Xaa Arg Ser Glu Thr Ala
1               5

<210> SEQ ID NO 101
<211> LENGTH: 3
<212> TYPE: PRT
<213> ORGANISM: Artificial Sequence
<220> FEATURE:
<223> OTHER INFORMATION: prion-binding ligand

<400> SEQUENCE: 101

Ile His Asn
1

<210> SEQ ID NO 102
<211> LENGTH: 3
<212> TYPE: PRT
<213> ORGANISM: Artificial Sequence
<220> FEATURE:
<223> OTHER INFORMATION: prion-binding ligand

<400> SEQUENCE: 102

Trp Glu Tyr
1

<210> SEQ ID NO 103
<211> LENGTH: 3
<212> TYPE: PRT
<213> ORGANISM: Artificial Sequence
<220> FEATURE:
<223> OTHER INFORMATION: prion-binding ligand

<400> SEQUENCE: 103

Asp Tyr Trp
1

<210> SEQ ID NO 104
<211> LENGTH: 3
<212> TYPE: PRT
<213> ORGANISM: Artificial Sequence
<220> FEATURE:
<223> OTHER INFORMATION: prion-binding ligand

<400> SEQUENCE: 104

Trp Asp Trp
1

<210> SEQ ID NO 105
<211> LENGTH: 3

```
<212> TYPE: PRT
<213> ORGANISM: Artificial Sequence
<220> FEATURE:
<223> OTHER INFORMATION: prion-binding ligand

<400> SEQUENCE: 105

Trp Gln Asp
1

<210> SEQ ID NO 106
<211> LENGTH: 3
<212> TYPE: PRT
<213> ORGANISM: Artificial Sequence
<220> FEATURE:
<223> OTHER INFORMATION: prion-binding ligand

<400> SEQUENCE: 106

Tyr Phe Glu
1

<210> SEQ ID NO 107
<211> LENGTH: 3
<212> TYPE: PRT
<213> ORGANISM: Artificial Sequence
<220> FEATURE:
<223> OTHER INFORMATION: prion-binding ligand

<400> SEQUENCE: 107

Asn Tyr Glu
1

<210> SEQ ID NO 108
<211> LENGTH: 3
<212> TYPE: PRT
<213> ORGANISM: Artificial Sequence
<220> FEATURE:
<223> OTHER INFORMATION: prion-binding ligand

<400> SEQUENCE: 108

Ser Tyr Ala
1

<210> SEQ ID NO 109
<211> LENGTH: 3
<212> TYPE: PRT
<213> ORGANISM: Artificial Sequence
<220> FEATURE:
<223> OTHER INFORMATION: prion-binding ligand

<400> SEQUENCE: 109

Trp Asp Leu
1

<210> SEQ ID NO 110
<211> LENGTH: 3
<212> TYPE: PRT
<213> ORGANISM: Artificial Sequence
<220> FEATURE:
<223> OTHER INFORMATION: prion-binding ligand

<400> SEQUENCE: 110

Trp Leu Glu
1

<210> SEQ ID NO 111
<211> LENGTH: 3
<212> TYPE: PRT
```

-continued

```
<213> ORGANISM: Artificial Sequence
<220> FEATURE:
<223> OTHER INFORMATION: prion-binding ligand

<400> SEQUENCE: 111

Val Gln Arg
1

<210> SEQ ID NO 112
<211> LENGTH: 3
<212> TYPE: PRT
<213> ORGANISM: Artificial Sequence
<220> FEATURE:
<223> OTHER INFORMATION: prion-binding ligand

<400> SEQUENCE: 112

Tyr Ile Asp
1

<210> SEQ ID NO 113
<211> LENGTH: 3
<212> TYPE: PRT
<213> ORGANISM: Artificial Sequence
<220> FEATURE:
<223> OTHER INFORMATION: prion-binding ligand

<400> SEQUENCE: 113

Arg Trp Asp
1

<210> SEQ ID NO 114
<211> LENGTH: 3
<212> TYPE: PRT
<213> ORGANISM: Artificial Sequence
<220> FEATURE:
<223> OTHER INFORMATION: prion-binding ligand

<400> SEQUENCE: 114

Asp Val Arg
1

<210> SEQ ID NO 115
<211> LENGTH: 3
<212> TYPE: PRT
<213> ORGANISM: Artificial Sequence
<220> FEATURE:
<223> OTHER INFORMATION: prion-binding ligand

<400> SEQUENCE: 115

Trp Ser Asp
1

<210> SEQ ID NO 116
<211> LENGTH: 3
<212> TYPE: PRT
<213> ORGANISM: Artificial Sequence
<220> FEATURE:
<223> OTHER INFORMATION: prion-binding ligand

<400> SEQUENCE: 116

His Trp Asp
1

<210> SEQ ID NO 117
<211> LENGTH: 3
<212> TYPE: PRT
<213> ORGANISM: Artificial Sequence
```

```
-continued

<220> FEATURE:
<223> OTHER INFORMATION: prion-binding ligand

<400> SEQUENCE: 117

Trp Gln Asp
1

<210> SEQ ID NO 118
<211> LENGTH: 3
<212> TYPE: PRT
<213> ORGANISM: Artificial Sequence
<220> FEATURE:
<223> OTHER INFORMATION: prion-binding ligand

<400> SEQUENCE: 118

Trp Asp Asp
1

<210> SEQ ID NO 119
<211> LENGTH: 3
<212> TYPE: PRT
<213> ORGANISM: Artificial Sequence
<220> FEATURE:
<223> OTHER INFORMATION: prion-binding ligand

<400> SEQUENCE: 119

Trp Glu Asp
1

<210> SEQ ID NO 120
<211> LENGTH: 3
<212> TYPE: PRT
<213> ORGANISM: Artificial Sequence
<220> FEATURE:
<223> OTHER INFORMATION: prion-binding ligand

<400> SEQUENCE: 120

Ile Thr Asn
1

<210> SEQ ID NO 121
<211> LENGTH: 3
<212> TYPE: PRT
<213> ORGANISM: Artificial Sequence
<220> FEATURE:
<223> OTHER INFORMATION: prion-binding ligand

<400> SEQUENCE: 121

Tyr Glu Asp
1

<210> SEQ ID NO 122
<211> LENGTH: 7
<212> TYPE: PRT
<213> ORGANISM: Artificial Sequence
<220> FEATURE:
<223> OTHER INFORMATION: prion-binding ligand

<400> SEQUENCE: 122

Arg Val Ala Asp Glu Glu Ala
1               5

<210> SEQ ID NO 123
<211> LENGTH: 7
<212> TYPE: PRT
<213> ORGANISM: Artificial Sequence
<220> FEATURE:
```

-continued

```
<223> OTHER INFORMATION: prion-binding ligand

<400> SEQUENCE: 123

Glu Tyr Tyr Val Asp Ala Ala
1               5

<210> SEQ ID NO 124
<211> LENGTH: 7
<212> TYPE: PRT
<213> ORGANISM: Artificial Sequence
<220> FEATURE:
<223> OTHER INFORMATION: prion-binding ligand

<400> SEQUENCE: 124

Trp Gln Asp Phe Asn Leu Ala
1               5

<210> SEQ ID NO 125
<211> LENGTH: 7
<212> TYPE: PRT
<213> ORGANISM: Artificial Sequence
<220> FEATURE:
<223> OTHER INFORMATION: prion-binding ligand

<400> SEQUENCE: 125

Tyr Asp Asn Pro Ile Asp Ala
1               5

<210> SEQ ID NO 126
<211> LENGTH: 7
<212> TYPE: PRT
<213> ORGANISM: Artificial Sequence
<220> FEATURE:
<223> OTHER INFORMATION: prion-binding ligand

<400> SEQUENCE: 126

Tyr Phe Asn Glu His Glu Ala
1               5

<210> SEQ ID NO 127
<211> LENGTH: 7
<212> TYPE: PRT
<213> ORGANISM: Artificial Sequence
<220> FEATURE:
<223> OTHER INFORMATION: prion-binding ligand

<400> SEQUENCE: 127

Glu Trp Gly Ala Asp Gly Ala
1               5

<210> SEQ ID NO 128
<211> LENGTH: 7
<212> TYPE: PRT
<213> ORGANISM: Artificial Sequence
<220> FEATURE:
<223> OTHER INFORMATION: prion-binding ligand

<400> SEQUENCE: 128

Asp Val Ile Tyr Ser His Ala
1               5

<210> SEQ ID NO 129
<211> LENGTH: 7
<212> TYPE: PRT
<213> ORGANISM: Artificial Sequence
<220> FEATURE:
<223> OTHER INFORMATION: prion-binding ligand
```

-continued

```
<400> SEQUENCE: 129

Trp His Ile Leu Glu Glu Ala
1               5

<210> SEQ ID NO 130
<211> LENGTH: 7
<212> TYPE: PRT
<213> ORGANISM: Artificial Sequence
<220> FEATURE:
<223> OTHER INFORMATION: prion-binding ligand

<400> SEQUENCE: 130

Asn Pro His Glu Asn Phe Ala
1               5

<210> SEQ ID NO 131
<211> LENGTH: 7
<212> TYPE: PRT
<213> ORGANISM: Artificial Sequence
<220> FEATURE:
<223> OTHER INFORMATION: prion-binding ligand

<400> SEQUENCE: 131

His Glu Asp Asn Gly Gly Ala
1               5

<210> SEQ ID NO 132
<211> LENGTH: 7
<212> TYPE: PRT
<213> ORGANISM: Artificial Sequence
<220> FEATURE:
<223> OTHER INFORMATION: prion-binding ligand

<400> SEQUENCE: 132

Ser Asp Ser Glu Gly Pro Ala
1               5

<210> SEQ ID NO 133
<211> LENGTH: 7
<212> TYPE: PRT
<213> ORGANISM: Artificial Sequence
<220> FEATURE:
<223> OTHER INFORMATION: prion-binding ligand

<400> SEQUENCE: 133

Glu Phe Gln Glu Phe Thr Ala
1               5

<210> SEQ ID NO 134
<211> LENGTH: 7
<212> TYPE: PRT
<213> ORGANISM: Artificial Sequence
<220> FEATURE:
<223> OTHER INFORMATION: prion-binding ligand

<400> SEQUENCE: 134

Gln Glu Gly Asp Glu Ile Ala
1               5

<210> SEQ ID NO 135
<211> LENGTH: 7
<212> TYPE: PRT
<213> ORGANISM: Artificial Sequence
<220> FEATURE:
<223> OTHER INFORMATION: prion-binding ligand
```

```
<400> SEQUENCE: 135

Asp Ile Tyr Ala Glu Thr Ala
1               5

<210> SEQ ID NO 136
<211> LENGTH: 7
<212> TYPE: PRT
<213> ORGANISM: Artificial Sequence
<220> FEATURE:
<223> OTHER INFORMATION: prion-binding ligand

<400> SEQUENCE: 136

Asp Arg Val Arg Glu Thr Ala
1               5

<210> SEQ ID NO 137
<211> LENGTH: 7
<212> TYPE: PRT
<213> ORGANISM: Artificial Sequence
<220> FEATURE:
<223> OTHER INFORMATION: prion-binding ligand

<400> SEQUENCE: 137

Phe Glu Glu Pro Gln Trp Ala
1               5

<210> SEQ ID NO 138
<211> LENGTH: 7
<212> TYPE: PRT
<213> ORGANISM: Artificial Sequence
<220> FEATURE:
<223> OTHER INFORMATION: prion-binding ligand

<400> SEQUENCE: 138

Phe Glu Gly Glu Glu Phe Ala
1               5

<210> SEQ ID NO 139
<211> LENGTH: 6
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (1)..(1)
<223> OTHER INFORMATION: Xaa at position 1 is either Thr or Leu

<400> SEQUENCE: 139

Xaa Phe Asn Ile His Ala
1               5

<210> SEQ ID NO 140
<211> LENGTH: 3
<212> TYPE: PRT
<213> ORGANISM: Artificial Sequence
<220> FEATURE:
<223> OTHER INFORMATION: prion-binding ligand

<400> SEQUENCE: 140

Tyr Asp Trp
1

<210> SEQ ID NO 141
<211> LENGTH: 3
<212> TYPE: PRT
<213> ORGANISM: Artificial Sequence
```

```
<220> FEATURE:
<223> OTHER INFORMATION: prion-binding ligand

<400> SEQUENCE: 141

Asn Tyr Thr
1

<210> SEQ ID NO 142
<211> LENGTH: 3
<212> TYPE: PRT
<213> ORGANISM: Artificial Sequence
<220> FEATURE:
<223> OTHER INFORMATION: prion-binding ligand

<400> SEQUENCE: 142

Ser Tyr Thr
1

<210> SEQ ID NO 143
<211> LENGTH: 3
<212> TYPE: PRT
<213> ORGANISM: Artificial Sequence
<220> FEATURE:
<223> OTHER INFORMATION: prion-binding ligand

<400> SEQUENCE: 143

Trp Ala Asp
1

<210> SEQ ID NO 144
<211> LENGTH: 3
<212> TYPE: PRT
<213> ORGANISM: Artificial Sequence
<220> FEATURE:
<223> OTHER INFORMATION: prion-binding ligand

<400> SEQUENCE: 144

Gln Trp Gly
1

<210> SEQ ID NO 145
<211> LENGTH: 3
<212> TYPE: PRT
<213> ORGANISM: Artificial Sequence
<220> FEATURE:
<223> OTHER INFORMATION: prion-binding ligand

<400> SEQUENCE: 145

Trp Gly Asp
1

<210> SEQ ID NO 146
<211> LENGTH: 3
<212> TYPE: PRT
<213> ORGANISM: Artificial Sequence
<220> FEATURE:
<223> OTHER INFORMATION: prion-binding ligand

<400> SEQUENCE: 146

Glu Tyr Phe
1

<210> SEQ ID NO 147
<211> LENGTH: 3
<212> TYPE: PRT
<213> ORGANISM: Artificial Sequence
<220> FEATURE:
```

-continued

<223> OTHER INFORMATION: prion-binding ligand

<400> SEQUENCE: 147

Trp Glu His
1

<210> SEQ ID NO 148
<211> LENGTH: 3
<212> TYPE: PRT
<213> ORGANISM: Artificial Sequence
<220> FEATURE:
<223> OTHER INFORMATION: prion-binding ligand

<400> SEQUENCE: 148

Leu Tyr Asp
1

<210> SEQ ID NO 149
<211> LENGTH: 3
<212> TYPE: PRT
<213> ORGANISM: Artificial Sequence
<220> FEATURE:
<223> OTHER INFORMATION: prion-binding ligand

<400> SEQUENCE: 149

Asp Tyr Tyr
1

<210> SEQ ID NO 150
<211> LENGTH: 3
<212> TYPE: PRT
<213> ORGANISM: Artificial Sequence
<220> FEATURE:
<223> OTHER INFORMATION: prion-binding ligand

<400> SEQUENCE: 150

Phe Tyr Glu
1

<210> SEQ ID NO 151
<211> LENGTH: 3
<212> TYPE: PRT
<213> ORGANISM: Artificial Sequence
<220> FEATURE:
<223> OTHER INFORMATION: prion-binding ligand

<400> SEQUENCE: 151

Glu Tyr Tyr
1

<210> SEQ ID NO 152
<211> LENGTH: 3
<212> TYPE: PRT
<213> ORGANISM: Artificial Sequence
<220> FEATURE:
<223> OTHER INFORMATION: prion-binding ligand

<400> SEQUENCE: 152

Tyr Asp Tyr
1

<210> SEQ ID NO 153
<211> LENGTH: 3
<212> TYPE: PRT
<213> ORGANISM: Artificial Sequence
<220> FEATURE:
<223> OTHER INFORMATION: prion-binding ligand

```
<400> SEQUENCE: 153

Trp Asp His
1

<210> SEQ ID NO 154
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (4)..(4)
<223> OTHER INFORMATION: Xaa at position 4 is 2-naphthyl-alanine

<400> SEQUENCE: 154

Arg Glu Ser Xaa Asn Val Ala
1               5

<210> SEQ ID NO 155
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (3)..(3)
<223> OTHER INFORMATION: Xaa at position 3 is 2-naphthyl-alanine

<400> SEQUENCE: 155

Glu Ser Xaa Pro Arg Gln Ala
1               5

<210> SEQ ID NO 156
<211> LENGTH: 7
<212> TYPE: PRT
<213> ORGANISM: Artificial Sequence
<220> FEATURE:
<223> OTHER INFORMATION: prion-binding ligand

<400> SEQUENCE: 156

Val Ala Arg Glu Asn Ile Ala
1               5

<210> SEQ ID NO 157
<211> LENGTH: 7
<212> TYPE: PRT
<213> ORGANISM: Artificial Sequence
<220> FEATURE:
<223> OTHER INFORMATION: prion-binding ligand

<400> SEQUENCE: 157

Arg Trp Glu Arg Glu Asp Ala
1               5

<210> SEQ ID NO 158
<211> LENGTH: 6
<212> TYPE: PRT
<213> ORGANISM: Artificial Sequence
<220> FEATURE:
<223> OTHER INFORMATION: prion-binding ligand

<400> SEQUENCE: 158

Glu Trp Trp Glu Thr Val
1               5
```

```
<210> SEQ ID NO 159
<211> LENGTH: 7
<212> TYPE: PRT
<213> ORGANISM: Artificial Sequence
<220> FEATURE:
<223> OTHER INFORMATION: prion-binding ligand

<400> SEQUENCE: 159

Ser Val Tyr Gln Leu Asp Ala
1               5

<210> SEQ ID NO 160
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (1)..(1)
<223> OTHER INFORMATION: Xaa at position 1 is 2-naphthyl-alanine

<400> SEQUENCE: 160

Xaa His Glu Phe Tyr Gly Ala
1               5

<210> SEQ ID NO 161
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (3)..(3)
<223> OTHER INFORMATION: Xaa at position 3 is 2-naphthyl-alanine
<220> FEATURE:
<221> NAME/KEY: MISC_FEATURE
<222> LOCATION: (4)..(4)
<223> OTHER INFORMATION: Xaa at position 4 is 2-naphthyl-alanine

<400> SEQUENCE: 161

His Glu Xaa Xaa Leu Val Ala
1               5

<210> SEQ ID NO 162
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (2)..(2)
<223> OTHER INFORMATION: Xaa at position 2 is 2-naphthyl-alanine
<220> FEATURE:
<221> NAME/KEY: MISC_FEATURE
<222> LOCATION: (6)..(6)
<223> OTHER INFORMATION: Xaa at position 6 is 2-naphthyl-alanine

<400> SEQUENCE: 162

Ala Xaa Val Pro Val Xaa Ala
1               5

<210> SEQ ID NO 163
<211> LENGTH: 7
<212> TYPE: PRT
<213> ORGANISM: Artificial Sequence
<220> FEATURE:
<223> OTHER INFORMATION: prion-binding ligand
```

```
<400> SEQUENCE: 163

Tyr Phe Asp Tyr Trp Leu Ala
1               5

<210> SEQ ID NO 164
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (3)..(3)
<223> OTHER INFORMATION: Xaa at position 3 is 2-naphthyl-alanine

<400> SEQUENCE: 164

Phe Glu Xaa His Arg Gln Ala
1               5

<210> SEQ ID NO 165
<211> LENGTH: 7
<212> TYPE: PRT
<213> ORGANISM: Artificial Sequence
<220> FEATURE:
<223> OTHER INFORMATION: prion-binding ligand

<400> SEQUENCE: 165

Trp Arg His Glu Pro Ala Ala
1               5

<210> SEQ ID NO 166
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (3)..(3)
<223> OTHER INFORMATION: Xaa at position 3 is 2-naphthyl-alanine

<400> SEQUENCE: 166

Ser Ser Xaa Lys Lys Asp Ala
1               5

<210> SEQ ID NO 167
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (2)..(2)
<223> OTHER INFORMATION: Xaa at position 2 is 2-naphthyl-alanine

<400> SEQUENCE: 167

Arg Xaa Asp Lys Glu Ala Ala
1               5

<210> SEQ ID NO 168
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
```

-continued

```
<222> LOCATION: (1)..(1)
<223> OTHER INFORMATION: Xaa at position 1 is 2-naphthyl-alanine

<400> SEQUENCE: 168

Xaa His Glu Ile Phe Pro Ala
1               5

<210> SEQ ID NO 169
<211> LENGTH: 7
<212> TYPE: PRT
<213> ORGANISM: Artificial Sequence
<220> FEATURE:
<223> OTHER INFORMATION: prion-binding ligand

<400> SEQUENCE: 169

Lys Trp Tyr His His Arg Ala
1               5

<210> SEQ ID NO 170
<211> LENGTH: 7
<212> TYPE: PRT
<213> ORGANISM: Artificial Sequence
<220> FEATURE:
<223> OTHER INFORMATION: prion-binding ligand

<400> SEQUENCE: 170

His Trp Trp Pro His Asn Ala
1               5

<210> SEQ ID NO 171
<211> LENGTH: 7
<212> TYPE: PRT
<213> ORGANISM: Artificial Sequence
<220> FEATURE:
<223> OTHER INFORMATION: prion-binding ligand

<400> SEQUENCE: 171

His Trp Gln Val Phe Tyr Ala
1               5

<210> SEQ ID NO 172
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (4)..(4)
<223> OTHER INFORMATION: Xaa at position 4 is 2-naphthyl-alanine

<400> SEQUENCE: 172

Phe His Glu Xaa Glu Ile Ala
1               5

<210> SEQ ID NO 173
<211> LENGTH: 7
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (5)..(5)
<223> OTHER INFORMATION: Xaa at position 5 is 2-naphthyl-alanine

<400> SEQUENCE: 173

His Ala Asp Phe Xaa Gln Ala
```

```
<210> SEQ ID NO 174
<211> LENGTH: 7
<212> TYPE: PRT
<213> ORGANISM: Artificial Sequence
<220> FEATURE:
<223> OTHER INFORMATION: prion-binding ligand

<400> SEQUENCE: 174

Ala Leu His Phe Glu Thr Ala
1               5

<210> SEQ ID NO 175
<211> LENGTH: 7
<212> TYPE: PRT
<213> ORGANISM: Artificial Sequence
<220> FEATURE:
<223> OTHER INFORMATION: prion-binding ligand

<400> SEQUENCE: 175

Asp Asp Pro Thr Gly Phe Ala
1               5

<210> SEQ ID NO 176
<211> LENGTH: 7
<212> TYPE: PRT
<213> ORGANISM: Artificial Sequence
<220> FEATURE:
<223> OTHER INFORMATION: prion-binding ligand

<400> SEQUENCE: 176

Val Ala Pro Gly Leu Gly Ala
1               5

<210> SEQ ID NO 177
<211> LENGTH: 7
<212> TYPE: PRT
<213> ORGANISM: Artificial Sequence
<220> FEATURE:
<223> OTHER INFORMATION: prion-binding ligand

<400> SEQUENCE: 177

Ile Phe Arg Leu Ile Glu Ala
1               5

<210> SEQ ID NO 178
<211> LENGTH: 7
<212> TYPE: PRT
<213> ORGANISM: Artificial Sequence
<220> FEATURE:
<223> OTHER INFORMATION: prion-binding ligand

<400> SEQUENCE: 178

Gly Leu Glu Arg Pro Glu Ala
1               5

<210> SEQ ID NO 179
<211> LENGTH: 7
<212> TYPE: PRT
<213> ORGANISM: Artificial Sequence
<220> FEATURE:
<223> OTHER INFORMATION: prion-binding ligand

<400> SEQUENCE: 179

Ile Val Val Arg Leu Trp Ala
1               5
```

```
<210> SEQ ID NO 180
<211> LENGTH: 7
<212> TYPE: PRT
<213> ORGANISM: Artificial Sequence
<220> FEATURE:
<223> OTHER INFORMATION: prion-binding ligand

<400> SEQUENCE: 180

Trp His Asn Pro His Tyr Ala
1               5

<210> SEQ ID NO 181
<211> LENGTH: 7
<212> TYPE: PRT
<213> ORGANISM: Artificial Sequence
<220> FEATURE:
<223> OTHER INFORMATION: prion-binding ligand

<400> SEQUENCE: 181

Leu Ile Tyr Lys Ser Asp Ala
1               5

<210> SEQ ID NO 182
<211> LENGTH: 7
<212> TYPE: PRT
<213> ORGANISM: Artificial Sequence
<220> FEATURE:
<223> OTHER INFORMATION: prion-binding ligand

<400> SEQUENCE: 182

Glu Lys Pro Ile Phe Asn Ala
1               5

<210> SEQ ID NO 183
<211> LENGTH: 7
<212> TYPE: PRT
<213> ORGANISM: Artificial Sequence
<220> FEATURE:
<223> OTHER INFORMATION: prion-binding ligand

<400> SEQUENCE: 183

His Trp Ser Glu Pro Ala Ala
1               5

<210> SEQ ID NO 184
<211> LENGTH: 7
<212> TYPE: PRT
<213> ORGANISM: Artificial Sequence
<220> FEATURE:
<223> OTHER INFORMATION: prion-binding ligand

<400> SEQUENCE: 184

Gly His Asn Trp Lys Glu Ala
1               5

<210> SEQ ID NO 185
<211> LENGTH: 7
<212> TYPE: PRT
<213> ORGANISM: Artificial Sequence
<220> FEATURE:
<223> OTHER INFORMATION: prion-binding ligand

<400> SEQUENCE: 185

Tyr Trp His His Asp Asp Ala
1               5
```

```
<210> SEQ ID NO 186
<211> LENGTH: 7
<212> TYPE: PRT
<213> ORGANISM: Artificial Sequence
<220> FEATURE:
<223> OTHER INFORMATION: prion-binding ligand

<400> SEQUENCE: 186

Gly Tyr Pro Lys Glu Asn Ala
1               5

<210> SEQ ID NO 187
<211> LENGTH: 7
<212> TYPE: PRT
<213> ORGANISM: Artificial Sequence
<220> FEATURE:
<223> OTHER INFORMATION: prion-binding ligand

<400> SEQUENCE: 187

Pro Val Tyr Trp Leu Tyr Ala
1               5

<210> SEQ ID NO 188
<211> LENGTH: 7
<212> TYPE: PRT
<213> ORGANISM: Artificial Sequence
<220> FEATURE:
<223> OTHER INFORMATION: prion-binding ligand

<400> SEQUENCE: 188

Phe Gly Glu His Thr Pro Ala
1               5

<210> SEQ ID NO 189
<211> LENGTH: 7
<212> TYPE: PRT
<213> ORGANISM: Artificial Sequence
<220> FEATURE:
<223> OTHER INFORMATION: prion-binding ligand

<400> SEQUENCE: 189

Phe Gln Gly Thr Arg Glu Ala
1               5

<210> SEQ ID NO 190
<211> LENGTH: 7
<212> TYPE: PRT
<213> ORGANISM: Artificial Sequence
<220> FEATURE:
<223> OTHER INFORMATION: prion-binding ligand

<400> SEQUENCE: 190

Thr Gly Thr Asn Arg Tyr Ala
1               5

<210> SEQ ID NO 191
<211> LENGTH: 7
<212> TYPE: PRT
<213> ORGANISM: Artificial Sequence
<220> FEATURE:
<223> OTHER INFORMATION: prion-binding ligand

<400> SEQUENCE: 191

Lys Trp Ala Thr Arg Tyr Ala
1               5
```

```
<210> SEQ ID NO 192
<211> LENGTH: 7
<212> TYPE: PRT
<213> ORGANISM: Artificial Sequence
<220> FEATURE:
<223> OTHER INFORMATION: prion-binding ligand

<400> SEQUENCE: 192

Asn Ser Thr Lys Phe Asp Ala
1               5

<210> SEQ ID NO 193
<211> LENGTH: 7
<212> TYPE: PRT
<213> ORGANISM: Artificial Sequence
<220> FEATURE:
<223> OTHER INFORMATION: prion-binding ligand

<400> SEQUENCE: 193

Leu Ile Tyr Lys Glu Glu Ala
1               5

<210> SEQ ID NO 194
<211> LENGTH: 7
<212> TYPE: PRT
<213> ORGANISM: Artificial Sequence
<220> FEATURE:
<223> OTHER INFORMATION: prion-binding ligand

<400> SEQUENCE: 194

Glu His Ala Thr Tyr Arg Ala
1               5

<210> SEQ ID NO 195
<211> LENGTH: 3
<212> TYPE: PRT
<213> ORGANISM: Artificial Sequence
<220> FEATURE:
<223> OTHER INFORMATION: prion-binding ligand

<400> SEQUENCE: 195

His Asn Asp
1

<210> SEQ ID NO 196
<211> LENGTH: 3
<212> TYPE: PRT
<213> ORGANISM: Artificial Sequence
<220> FEATURE:
<223> OTHER INFORMATION: prion-binding ligand

<400> SEQUENCE: 196

His Glu Arg
1

<210> SEQ ID NO 197
<211> LENGTH: 3
<212> TYPE: PRT
<213> ORGANISM: Artificial Sequence
<220> FEATURE:
<223> OTHER INFORMATION: prion-binding ligand

<400> SEQUENCE: 197

His Gly Asp
1

<210> SEQ ID NO 198
```

-continued

```
<211> LENGTH: 3
<212> TYPE: PRT
<213> ORGANISM: Artificial Sequence
<220> FEATURE:
<223> OTHER INFORMATION: prion-binding ligand

<400> SEQUENCE: 198

His Ser Asp
1

<210> SEQ ID NO 199
<211> LENGTH: 3
<212> TYPE: PRT
<213> ORGANISM: Artificial Sequence
<220> FEATURE:
<223> OTHER INFORMATION: prion-binding ligand

<400> SEQUENCE: 199

His Phe Asp
1

<210> SEQ ID NO 200
<211> LENGTH: 3
<212> TYPE: PRT
<213> ORGANISM: Artificial Sequence
<220> FEATURE:
<223> OTHER INFORMATION: prion-binding ligand

<400> SEQUENCE: 200

Trp Asn Asp
1

<210> SEQ ID NO 201
<211> LENGTH: 3
<212> TYPE: PRT
<213> ORGANISM: Artificial Sequence
<220> FEATURE:
<223> OTHER INFORMATION: prion-binding ligand

<400> SEQUENCE: 201

Tyr Glu His
1

<210> SEQ ID NO 202
<211> LENGTH: 3
<212> TYPE: PRT
<213> ORGANISM: Artificial Sequence
<220> FEATURE:
<223> OTHER INFORMATION: prion-binding ligand

<400> SEQUENCE: 202

His Trp Asp
1

<210> SEQ ID NO 203
<211> LENGTH: 3
<212> TYPE: PRT
<213> ORGANISM: Artificial Sequence
<220> FEATURE:
<223> OTHER INFORMATION: prion-binding ligand

<400> SEQUENCE: 203

Tyr His Asp
1

<210> SEQ ID NO 204
<211> LENGTH: 3
```

```
<212> TYPE: PRT
<213> ORGANISM: Artificial Sequence
<220> FEATURE:
<223> OTHER INFORMATION: prion-binding ligand

<400> SEQUENCE: 204

Tyr Asp Trp
1

<210> SEQ ID NO 205
<211> LENGTH: 3
<212> TYPE: PRT
<213> ORGANISM: Artificial Sequence
<220> FEATURE:
<223> OTHER INFORMATION: prion-binding ligand

<400> SEQUENCE: 205

Trp Asp Tyr
1

<210> SEQ ID NO 206
<211> LENGTH: 3
<212> TYPE: PRT
<213> ORGANISM: Artificial Sequence
<220> FEATURE:
<223> OTHER INFORMATION: prion-binding ligand

<400> SEQUENCE: 206

His Tyr Asp
1

<210> SEQ ID NO 207
<211> LENGTH: 3
<212> TYPE: PRT
<213> ORGANISM: Artificial Sequence
<220> FEATURE:
<223> OTHER INFORMATION: prion-binding ligand

<400> SEQUENCE: 207

His Trp Asp
1

<210> SEQ ID NO 208
<211> LENGTH: 3
<212> TYPE: PRT
<213> ORGANISM: Artificial Sequence
<220> FEATURE:
<223> OTHER INFORMATION: prion-binding ligand

<400> SEQUENCE: 208

Trp Thr Asp
1

<210> SEQ ID NO 209
<211> LENGTH: 3
<212> TYPE: PRT
<213> ORGANISM: Artificial Sequence
<220> FEATURE:
<223> OTHER INFORMATION: prion-binding ligand

<400> SEQUENCE: 209

Phe Pro Lys
1

<210> SEQ ID NO 210
<211> LENGTH: 3
<212> TYPE: PRT
```

-continued

<213> ORGANISM: Artificial Sequence
<220> FEATURE:
<223> OTHER INFORMATION: prion-binding ligand

<400> SEQUENCE: 210

His Trp Lys
1

<210> SEQ ID NO 211
<211> LENGTH: 3
<212> TYPE: PRT
<213> ORGANISM: Artificial Sequence
<220> FEATURE:
<223> OTHER INFORMATION: prion-binding ligand

<400> SEQUENCE: 211

Trp Glu Glu
1

<210> SEQ ID NO 212
<211> LENGTH: 3
<212> TYPE: PRT
<213> ORGANISM: Artificial Sequence
<220> FEATURE:
<223> OTHER INFORMATION: prion-binding ligand

<400> SEQUENCE: 212

Leu Leu Arg
1

<210> SEQ ID NO 213
<211> LENGTH: 3
<212> TYPE: PRT
<213> ORGANISM: Artificial Sequence
<220> FEATURE:
<223> OTHER INFORMATION: prion-binding ligand

<400> SEQUENCE: 213

Ser Tyr Phe
1

<210> SEQ ID NO 214
<211> LENGTH: 3
<212> TYPE: PRT
<213> ORGANISM: Artificial Sequence
<220> FEATURE:
<223> OTHER INFORMATION: prion-binding ligand

<400> SEQUENCE: 214

Glu Tyr Tyr
1

<210> SEQ ID NO 215
<211> LENGTH: 7
<212> TYPE: PRT
<213> ORGANISM: Artificial Sequence
<220> FEATURE:
<223> OTHER INFORMATION: prion-binding ligand

<400> SEQUENCE: 215

Asp Arg Asp Leu Thr Phe Ala
1 5

<210> SEQ ID NO 216
<211> LENGTH: 7
<212> TYPE: PRT
<213> ORGANISM: Artificial Sequence

```
<220> FEATURE:
<223> OTHER INFORMATION: prion-binding ligand

<400> SEQUENCE: 216

His Asn Trp Trp Ile Ile Ala
1               5

<210> SEQ ID NO 217
<211> LENGTH: 7
<212> TYPE: PRT
<213> ORGANISM: Artificial Sequence
<220> FEATURE:
<223> OTHER INFORMATION: prion-binding ligand

<400> SEQUENCE: 217

Glu Val Lys Ile Gly Asn Ala
1               5

<210> SEQ ID NO 218
<211> LENGTH: 3
<212> TYPE: PRT
<213> ORGANISM: Artificial Sequence
<220> FEATURE:
<223> OTHER INFORMATION: prion-binding ligand

<400> SEQUENCE: 218

Ser Ile Val
1

<210> SEQ ID NO 219
<211> LENGTH: 3
<212> TYPE: PRT
<213> ORGANISM: Artificial Sequence
<220> FEATURE:
<223> OTHER INFORMATION: prion-binding ligand

<400> SEQUENCE: 219

Ala Tyr Pro
1

<210> SEQ ID NO 220
<211> LENGTH: 8
<212> TYPE: PRT
<213> ORGANISM: Artificial Sequence
<220> FEATURE:
<223> OTHER INFORMATION: prion-binding ligand

<400> SEQUENCE: 220

Pro His Gly Gly Gly Trp Gly Gln
1               5

<210> SEQ ID NO 221
<211> LENGTH: 5
<212> TYPE: PRT
<213> ORGANISM: prion sp.
<220> FEATURE:
<221> NAME/KEY: MISC_FEATURE
<222> LOCATION: (4)..(4)
<223> OTHER INFORMATION: Xaa at position 4 is Gly, Pro or Asn

<400> SEQUENCE: 221

Arg Tyr Pro Xaa Gln
1               5

<210> SEQ ID NO 222
<211> LENGTH: 6
<212> TYPE: PRT
```

```
<213> ORGANISM: prion sp.
<220> FEATURE:
<221> NAME/KEY: MISC_FEATURE
<222> LOCATION: (1)..(1)
<223> OTHER INFORMATION: Xaa at position 1 is any amino acid
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (5)..(5)
<223> OTHER INFORMATION: Xaa at position 5 is Arg or Gln
<220> FEATURE:
<221> NAME/KEY: MISC_FEATURE
<222> LOCATION: (6)..(6)
<223> OTHER INFORMATION: Xaa at position 6 is any amino acid

<400> SEQUENCE: 222

Xaa Xaa Tyr Tyr Xaa Xaa
1               5

<210> SEQ ID NO 223
<211> LENGTH: 4
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (1)..(1)
<223> OTHER INFORMATION: Xaa at position 1 is Phe, Trp, or Tyr
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (3)..(3)
<223> OTHER INFORMATION: Xaa at position 3 is Asp or Glu
<220> FEATURE:
<221> NAME/KEY: MISC_FEATURE
<222> LOCATION: (4)..(4)
<223> OTHER INFORMATION: Xaa at position 4 is Phe, Trp, or Tyr

<400> SEQUENCE: 223

Xaa Xaa Xaa Xaa
1

<210> SEQ ID NO 224
<211> LENGTH: 4
<212> TYPE: PRT
<213> ORGANISM: Artificial Sequence
<220> FEATURE:
<223> OTHER INFORMATION: prion-binding ligand
<220> FEATURE:
<221> NAME/KEY: MISC_FEATURE
<222> LOCATION: (1)..(1)
<223> OTHER INFORMATION: Xaa at position 1 is Phe, Trp or Tyr
<220> FEATURE:
<221> NAME/KEY: MISC_FEATURE
<222> LOCATION: (2)..(2)
<223> OTHER INFORMATION: Xaa at position 2 is Asp or Glu
<220> FEATURE:
<221> NAME/KEY: MISC_FEATURE
<222> LOCATION: (3)..(3)
<223> OTHER INFORMATION: Xaa at position 3 is any amino acid
<220> FEATURE:
<221> NAME/KEY: MISC_FEATURE
<222> LOCATION: (4)..(4)
<223> OTHER INFORMATION: Xaa at position 4 is Phe, Trp or Tyr

<400> SEQUENCE: 224

Xaa Xaa Xaa Xaa
```

-continued

```
<210> SEQ ID NO 225
<211> LENGTH: 5
<212> TYPE: PRT
<213> ORGANISM: Artificial Sequence
<220> FEATURE:
<223> OTHER INFORMATION: Prion-binding ligand

<400> SEQUENCE: 225

Trp Phe Val Glu Ala
1               5

<210> SEQ ID NO 226
<211> LENGTH: 7
<212> TYPE: PRT
<213> ORGANISM: Artificial Sequence
<220> FEATURE:
<223> OTHER INFORMATION: Prion-binding ligand
<220> FEATURE:
<221> NAME/KEY: MISC_FEATURE
<222> LOCATION: (4)..(4)
<223> OTHER INFORMATION: xaa = 2-naphthyl-alanine

<400> SEQUENCE: 226

Asp Glu Ser Xaa Pro Arg Gln
1               5
```

PRION PROTEIN LIGANDS AND METHODS OF USE

CROSS-REFERENCE TO RELATED APPLICATIONS

This application claims benefit of U.S. Provisional Patent Application Ser. No. 60/430,423 filed Dec. 3, 2002.

FIELD OF THE INVENTION

This invention relates to the field of protein-ligand interactions and more particularly relates to the identification of ligands that bind to prion proteins and methods of using the ligands to detect or remove prions from biological samples.

BACKGROUND OF THE INVENTION

Native or cellular prion protein "PrPc" is widely distributed throughout the mammalia and has a particularly well-conserved amino acid sequence and protein structure. Infectious prions are thought to be composed of a modified form of the normal cellular (PrPc) prion protein and are called "PrPsc". Prions have some properties in common with other infectious pathogens, but do not appear to contain nucleic acid. Instead, it is proposed that a post-translational conformational change is involved in the conversion of non-infectious PrPc into infectious PrPsc during which α-helices are transformed into β-sheets. PrPc contains three α-helices and has little β-sheet structure; in contrast, PrPsc is rich in β-sheet. The conversion of PrPc to PrPsc is believed to lead to the development of transmissible spongiform encephalopathies (TSEs) during which PrPsc accumulates in the central nervous system (CNS) and is accompanied by neuropathologic changes and neurological dysfunction. PrPsc, often referred to as the "scrapie" form of the prion protein, is considered necessary and possibly sufficient for the transmission and pathogenesis of these transmissible neurodegenerative diseases of animals and humans.

Specific examples of TSEs include scrapie, which affects sheep and goats; bovine spongiform encephalopathy (BSE), which affects cattle; transmissible mink encephalopathy, feline spongiform encephalopathy and chronic wasting disease (CWD) of mule deer, white-tailed deer, black-tailed deer and elk. In humans TSE diseases may present themselves as, kuru, Creutzfeldt-Jakob disease (CJD), Gerstmann-Straüssler-Scheinker Syndrome (GSS), fatal insomnia and variant Creutzfeldt-Jakob disease (vCJD). vCJD recently emerged in humans as a result of the BSE epidemic in Britain and is most probably caused by the consumption of food products derived from cattle infected with BSE or "mad cow disease". An unknown number of people in the UK ingested food potentially contaminated with nervous tissue from BSE-infected cattle during the mid 1980s to early 1990s. Because the incubation period for the orally contracted disease may be more than 20 years in humans, the true incidence of vCJD may not become apparent for many years. To date, over 130 people are known to have contracted the disease, primarily in the UK; however, cases have been reported in Canada, France, Hong Kong, Ireland, Italy, and the US. The export of contaminated bovine feed products from the UK worldwide indicates a possible global presence of BSE and hence the probability of vCJD. Consistent with these observations is the detection of BSE in most European countries, Japan and Israel. Consequently, the ability to detect and remove infectious prion protein from a variety of materials including food products is of profound importance.

Historically, the diagnosis of TSEs was based on the occurrence of clinical signs of the disease and could be confirmed only by post-mortem histological examination of brain tissue. A characteristic of all TSEs is the lack of a measurable host immune response to the agent. Thus, no antibodies are produced and no conventional serologic test can be used to identify infected animals. Recently, identification of abnormal prion protein in the brain has improved the ability to make a disease diagnosis.

In addition to ingestion of infected products of bovine origin, blood transfusion and organ transplantation represent another potential mode of transmission of vCJD among humans. The likelihood of transmissibility of vCJD in humans by blood transfusion is currently unknown, but based on data from experimental animal models including transmission from sheep experimentally infected orally with BSE and sheep naturally infected with scrapie, appears to be a very likely possibility. Unlike other human TSEs, PrPsc is present in the lymphoreticular system of vCJD patients, thereby increasing the probability of the infectious agent being in blood and its transmission through blood transfusion. Other factors elevating concern about the risk of transmission by transfusion include the unknown, but presumably high, numbers of people exposed to BSE and lack of a preclinical diagnostic test for vCJD. Moreover, the virulence of vCJD appears to be enhanced following species adaptation in primates and mice, suggesting that human to human transmission may be more efficient than cow to human. Thus, there is an urgent need for methods to prevent the transmission of vCJD by blood transfusion. Such measures may include early identification of infected donors and their deferral, removal and inactivation of TSE agents in animal derived food and health products intended for animal or human consumption or applications, human and bovine derived blood-derived products, and organ transplants. Unfortunately, PrPsc is remarkably resistant to chemical and physical methods of inactivation, and a selective method of inactivation is elusive.

Prion removal through the specific interaction with ligands appears more promising. A number of ligands have already been identified that bind to prion protein. Combinatorial peptide libraries have been screened for ligands that bind to the octapeptide repeat sequence (PHGGGWGQ (SEQ ID NO:220)) found in all known mammalian prion proteins and a series of ligands were discovered, as described in PCT/US01/11150. Other materials include a variety of polymers, for example, amino polymethacrylate from TosoBioSep, ion exchange resins generally (see U.S. Pat. No. 5,808,011 to Gawryl et al.), ligands that interact with amyloid plaque for example, Congo Red (Ingrosso, L., et al., Congo red prolongs the incubation period in scrapie-infected hamsters. *J. Virology* 69:506-508 (1995)), 4-iodo, 4-deoxy doxorubicin (Tagliavini, F., et al., Effectiveness of anthracycline against experimental prion diseases in Syrian hamsters. *Science* 276: 1119-1122 (1997)), amphotericin B, porphyrins and phthalocyanines (Priola, S. A., et al., Porphyrin and Phthalocyanine antiscrapie compounds, *Science* 287:1503-1506 (2000)), metals (Stockel et al., *Biochemistry,* 37, 7185-7193 (1998)), peptides that interact with PrP to form complexes (see U.S. Pat. No. 5,750,361 to Prusiner et al. and Soto, C. et al., Reversion of prion protein conformational changes in synthetic β-sheet breaker peptides, *Lancet,* 355:192-197 (2000)), heparin and other polysulphated polyanions (Caughey, B., et al., Binding of the Protease-sensitive form of prion protein PrP to Sulphated Glycosaminoglycan and Congo Red, *J. Virology* 68:2135-2141(1994)), antibodies (Kascsak, R. J., et al., Immunodiagnosis of prion disease, *Immunological Invest.* 26:259-268 (1997)), and other proteins, e.g. plasminogen (Fischer, M. B. et al., Binding of disease-associated prion protein to plasminogen., *Nature* 408:479-483 (2000)). Currently, no ligand has been fully characterized or found to be able to bind to prion from a wide variety of media, although some may be useful in specific circumstances (see U.S. Pat. No. 5,808,011 to Gawryl et al.).

To date, human TSE diseases are 100% fatal. Unfortunately, even though a number of compounds including amphotericins, sulphated polyanions, Congo Red dye and anthracycline antibiotics have been reported as prospective therapeutic agents, all have demonstrated only modest potential to impede prion propagation, and none have been shown to have any effect on the removal of pre-existing prions from an infected host. Thus, there remains an urgent need for new therapeutic agents.

The assembly and disassembly of normally soluble proteins into conformationally altered and insoluble forms are thought to be a causative process in a variety of other diseases, many of which are neurological diseases. The relationship between the onset of the disease and the transition from the normal to the conformationally altered protein is poorly understood. Examples of such insoluble proteins in addition to prion include: β-amyloid peptide in amyloid plaques of Alzheimer's disease and cerebral amyloid angiopathy (CAA); α-synuclein deposits in Lewy bodies of Parkinson's disease, tau in neurofibrillary tangles in frontal temporal dementia and Pick's disease; superoxide dismutase in amyotrophic lateral sclerosis; and huntingtin in Huntington's Disease.

Often these highly insoluble proteins form aggregates composed of non-branching fibrils with the common characteristic of a β-pleated sheet conformation. In the central nervous system, amyloid can be present in cerebral and menningeal blood vessels (cerebrovascular deposits) and in brain parenchyma (plaques). Neuropathological studies in human and animal models indicate that cells proximal to amyloid deposits are disturbed in their normal functions.

The precise mechanism by which neuritic plaques are formed and the relationship of plaque formation to the disease-associated neurodegenerative processes are largely unknown. Methodologies that can readily separate or that can distinguish between two or more different conformational forms of a protein, for example, PrPc and PrPsc, are needed to understand the process of conversion and to find structures that will specifically interact with the disease associated form. Current methodologies for separating or distinguishing between isoforms include: differential mobility in polyacrylamide gels in the presence of a chaotrope such as urea, i.e., transverse urea gradient (TUG) gels; differential sensitivity to protease treatment, for example, proteinase K (PK) and the detection of the PK resistant digest product of PrPsc referred to a PrPres; differential temperature stability; relative solubility in non-ionic detergents; and the ability for fibrillar structures to bind certain chemicals, for example, Congo red and isoflavin S. However, there remains an unmet need to identify high affinity reagents that are specific for the conformationally altered protein and especially forms associated with disease. Such reagents would be useful for developing possible diagnostic kits, separation and purification of the different forms of protein, for removal of infectious forms of the disease from therapeutic agents, biological products, vaccines and foodstuffs, and for therapy.

SUMMARY OF THE INVENTION

Ligands that bind to prion proteins and their applications are provided. The ligands are peptides that bind with selectivity and specificity to prion analytes. The ligands are capable of binding to one or more forms of prion protein including cellular prion protein (PrPc), infectious prion protein (PrPsc), and recombinant prion protein (PrPr). Prions from various species, including humans and hamsters, are bound by the ligands. Compositions containing the prion protein binding ligands on a support such as a resin or a membrane are also provided.

The ligands are useful for detecting or removing a prion protein from a sample, such as a biological fluid or an environmental sample. The ligands are used to detect or remove all prion protein from the sample or can be selectively chosen to detect or remove a single form of prion protein and can therefore be used to distinguish between infectious and non-infectious prion protein in the sample from patients afflicted with human TSEs and animals afflicted with scrapie, BSE and CWD.

Also provided is a method of treating or retarding the development of a prion-associated pathology in a subject. For example, the ligands of the invention may be useful in treating pathologies such as CJD, vCJD, GSS, fatal insomnia, scrapie, BSE and CWD. Such ligands may act by inhibiting polymerization of PrPsc or through inhibiting the interaction of PrPsc and PrPc thereby slowing down the development of further PrPsc.

Another aspect of the invention provides a method for identifying additional ligands, particularly ligands specific for the conformationally altered forms of proteins, some of which are involved in the development of diseases. The described methodology is also appropriate for the discovery, evaluation or screening of large numbers of potential drug candidates that bind directly to PrPsc.

Other features and advantages of the invention will be apparent from the following detailed description and preferred embodiments.

BRIEF DESCRIPTION OF THE FIGURES

FIG. 2 FIGS. 2A-B Binding of huPrPc from extracts of normal human brain to affinity resins in a column format. Brain homogenate and beads were prepared and equilibrated in either phosphate (PBS) or citrate phosphate dextrose (CPD) buffers. The strength of the signal on the Western blots is a function of the strength of PrPc binding to the resin. Lane 1 contains molecular weight marker (MW); Lane 2, 20 µl of 0.1% normal human brain homogenate. Lane 3-8, PrPc eluted from beads.

FIG. 3 FIGS. 3A-B Binding of huPrPsc from extracts of CJD infected human brain to affinity resins in a batch format. The figures are Western blots that show the amount of prion eluted from beads following contact with a homogenate containing huPrPsc from a patient with sporadic CJD. The beads were washed following contact with the homogenate that were either treated with PK to reveal the presence of PrPres or remained untreated. They were boiled in buffer containing SDS to release bound protein, and the samples were resolved by SDS-PAGE followed by Western blotting. The binding of huPrPsc and PrPc to the resins is demonstrated by presence of PrP specific bands following probing with a monoclonal antibody, 3F4. Peptide sequences are indicated at the top of the gel. Samples digested with PK are identified as (+), undigested as (−).

FIGS. 6A-F Removal of PrPres from infected RBCCs by various affinity resins. Red Blood Cell Concentrates (RBCCs) were spiked with brain homogenate from hamsters infected with Scrapie and passed in succession through columns of resins with various affinity ligands. Resin-bound proteins were analyzed by gel electrophoresis. Gel loading pattern is shown in Table 11.

DETAILED DESCRIPTION

Ligands that bind to prion proteins and their applications are described herein. The ligands are proteins, peptides or polypeptides that bind with specificity and affinity to prion proteins. Preferably, the ligands have a molecular weight of 6 kDa or less.

The ligands are useful in methods for detecting prion protein in a sample, such as a human or animal derived biological fluid or an environmental sample, as well as methods for diagnosing and treating prion disease. For example, the ligands of the invention may be useful in treating diagnosing pathologies such as CJD, vCJD, GSS, fatal insomnia, scrapie, BSE and CWD and other TSEs using whole blood, blood components, cells, serum, plasma, plasma derivatives, cerebrospinal fluid, urine, tears tonsils, appendix and others. The ligands may also be useful for the removal of prion protein from a sample, such as a blood sample, blood components, cells, serum, plasma, plasma derivatives, cerebrospinal fluid, urine, tears tonsils, appendix and others. The ligands are used to detect or remove all prion protein from the sample or can be selectively chosen to detect or remove a single form of prion protein and can therefore be used to distinguish between infectious and non-infectious prion protein in the sample.

The methods described may be used for screening polymers, synthetic compounds and libraries of synthetic compounds for additional ligands to prions.

Also provided herein is a method for identifying additional ligands, particularly ligands specific for the conformationally altered forms of proteins, some of which are involved in the development of diseases.

Also provided is a methodology that is appropriate for the discovery, evaluation or screening of large numbers of potential drug candidates.

DEFINITIONS

The terms "a," "an" and "the" as used herein are defined to mean "one or more" and include the plural unless the context is inappropriate.

The term "3F4" refers to the monoclonal antibody specific to native forms of PrPc, but not native PrPsc or PrPres. The antibody has specificity for denatured forms of hamster and human PrPc, PrPsc and PrPres.

As used herein, the terms "blood-derived compositions" and blood compositions are used interchangeably and are meant to include whole blood, red blood cell concentrate, plasma, serum, platelet rich and platelet poor fractions, platelet concentrates, white blood cells, blood plasma precipitates, blood plasma fractionation precipitates and supernatants, immunoglobulin preparations including IgA, IgE, IgG and IgM, purified coagulation factor concentrates, fibrinogen concentrate, or various other compositions which are derived from humans or animals. It also includes purified blood derived proteins prepared by any of various methods common in the art including ion exchange, affinity, gel permeation, and/or hydrophobic chromatography or by differential precipitation.

The term "combinatorial library" refers to a collection of chemicals that have been synthesized by solid-phase combinatorial chemistry techniques. This definition encompasses using a split-couple-recombine method that generates millions of random peptides of a defined length or may be designed to include defined structures. The building blocks may be natural amino acids, synthetic molecules, amino acid analogs, branched analogs, triazine dyes, and the like.

The term "conservative variations" or "conservative modified variations" of a particular sequence refers to amino acids or other closely related structures that have substantial chemical similarity. Furthermore, individual substitutions, deletions or additions which alter, add or delete a single amino acid or a small percentage of amino acids in an encoded sequence are conservatively modified variations where the alterations result in the substitution of an amino acid with a chemically similar amino acid. Conservative substitution tables providing functionally similar amino acids are well known in the art. The following six groups each contain natural amino acids that are conservative substitutions for one another:

1) Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V), Alanine (A)
6) Phenylalanine (F), Tyrosine (Y), Tryptophan (W).

Numerous unnatural amino acids are also considered conservative substitutions of naturally occurring amino acids. Two polypeptides are said to be "identical" if the sequence of amino acid residues in the two sequences is the same when aligned for maximum correspondence. Optimal alignment of sequences for comparison may be conducted by the local homology algorithm of Smith and Waterman, *Adv. Appl. Math.* 2: 482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "ligand" refers to a molecule to which a protein, peptide or polypeptide binds. The ligands of the present invention can be antibody preparations, proteins, peptides, polypeptides, amino acids, nucleic acids, carbohydrates, sugars, lipids, organic molecules, polymers, and/or putative therapeutic agents, and the like.

Figure 1:
FIG. 1 Chemiluminescent signals from beads from a combinatorial library binding haPrPc and haPrPsc from brain homogenate. PrPc and PrPsc were detected through binding of a specific monoclonal antibody (3F4) and alkaline phosphatase conjugated secondary antibodies specific for 3F4. Light produced by a chemiluminescent substrate specific for alkaline phosphatase was detected on autoradiography film. The locations of signals generated from beads from a combinatorial library are numbered. The ligands on the beads were subsequently sequenced. These beads did not produce a signal prior to transfer and denaturation, but emitted a strong signal following transfer and denaturation of bound proteins and labeling with enzyme conjugate 3F4 antibody.
Figure 2A:
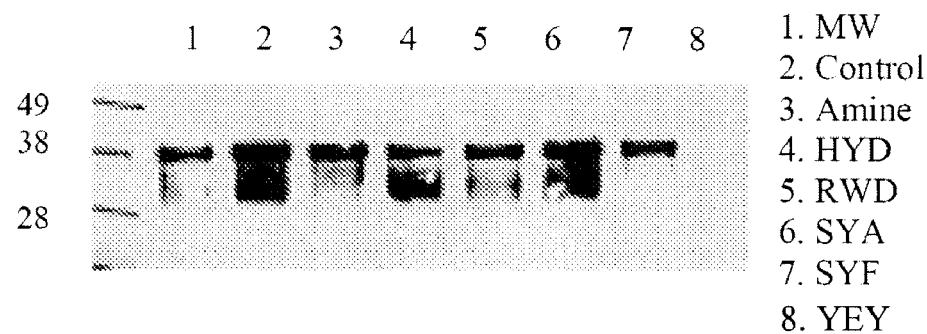
Figure 2B:
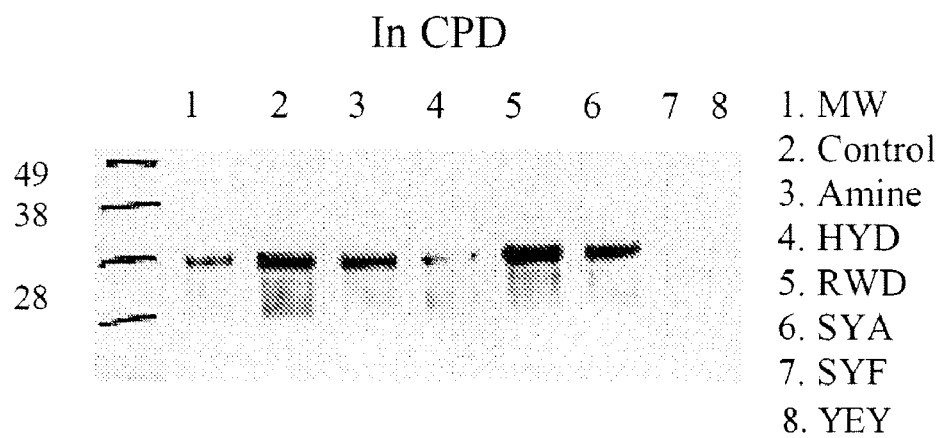

The terms "protein" "peptide," "polypeptide" and "oligopeptide" are used interchangeably and are defined herein as a chain of amino acids in which carbons are linked through peptide bonds formed by a condensation reaction between the carboxyl group of one amino acid and the amino group of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free amino group on the amino acid at the amino terminal of the peptide, or to the amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide. When synthesized on resin by Merrifield synthesis the C-terminal carboxyl group is coupled to the resin usually through a peptide bond to an immobilized amino group.

Typically, the amino acids making up a peptide are numbered in order, starting at the amino terminal and increasing in the direction of the carboxy terminal of the peptide. Thus, when one amino acid is said to "follow" another, that amino acid is positioned closer to the carboxy terminal of the peptide than the "preceding" amino acid.

The term "PrPc" refers to the native prion protein molecule which is naturally and widely expressed within the body of the Mammalia. Its structure is highly conserved and is not associated with a disease state.

The term "PrPsc" refers to the conformationally altered form of the PrPc molecule that is that is thought to be infectious and is associated with TSE/prion diseases, including vCJD, CJD, kuru, fatal insomnia, GSS, scrapie, BSE, CWD, and other rare TSEs of captive and experimental animals. It has the same amino acid sequence as normal, cellular PrPc, but has converted some of the α-helix to β-sheet and is associated with a disease state.

The term "PrPres" refers to the proteinase resistant derivatives of the PrPsc protein of 27-30 kDa that remain following partial digestion of PrPsc with PK.

The term "PrPr" refers to the prion protein expressed by recombinant technology.

The term "PrP" refers to prion protein in general.

The term "residue" is used herein to refer to an amino acid (D or L) or an amino acid mimetic that is incorporated into an oligopeptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The term "substantial identity" means that a polypeptide comprises a sequence that has at least 66% or more amino acids in common. Another indication that polypeptide sequences are substantially identical is if one peptide is immunologically reactive with antibodies raised against the disclosed peptide. Thus, the peptides of the invention include peptides and other chemicals immunologically reactive with antibodies raised against the disclosed immunogenic peptides.

The term "capable of binding" as used herein refers to binding of two or molecules to form a complex with each other, for example, binding of a ligand to a protein or a peptide, under conditions, wherein the two or more molecules are capable of forming a complex, such as a protein-ligand complex.

Ligands that Bind to a Particular Amino Acid Sequence of PrP

The prion-binding ligands described herein are all small molecules, preferably peptides. The ligands bind to peptides, polypeptides derived from the prion protein, or the entire prion molecule. As used herein, no particular length is implied by the term "peptide." Preferably, the ligands described herein bind to a prion protein having one or more of the following amino acid sequences:

RYPxQ (SEQ ID NO:221), wherein x is G, P or N
XxYYux (SEQ ID NO:222), wherein x is any amino acid, and u is R or Q More preferably the ligands bind to a prion protein having one or more of the following amino acid sequences:

```
RYPGQ          (SEQ ID NO: 1)
DRYYRD         (SEQ ID NO: 2)
QAYYQR         (SEQ ID NO: 3)
QVYYRP         (SEQ ID NO: 4)
```

Labelled peptides having one or more of the amino acid sequences provided above are useful when used to probe combinatorial libraries for ligands that bind to prions. Preferably, the peptides are radiolabelled and acetylated at the amino terminus and amidated at the carboxy terminus when used to screen libraries for prion ligands.

The amino acid sequence of the ligands described herein lack the amino acid sequences disclosed in WO 01/77687, which binds to the octapeptide repeat sequence of the prion protein.

In a first preferred embodiment, the ligand is a protein or peptide having an amino acid sequence that binds to SEQ ID NO:1. The amino acid sequences set forth in Table 1 below (SEQ ID NOS. 5-13) are examples of amino acid sequences that bind to SEQ ID NO:1. Therefore, ligands having one or more of the sequences set forth in Table 1 are included in the ligands of the first preferred embodiment. The amino acid sequences set forth in Table 1 were identified in a 6-mer library screened for 6-mers that bind to SEQ ID NO:1. The library was constructed with an alanine (A) as a spacer between the resin and the combinatorial peptides of the library and is represented as the final A in the sequences which is included in Table 1. It will be understood by those skilled in the art that the ligands provided herein are not limited to those having the exemplary sequences set forth in Table 1.

TABLE 1

Six-amino acid sequences binding to SEQ ID NO: 1

| SEQ ID NO | SEQUENCE |
|---|---|
| 5 | KIHKFLA |
| 6 | GTHDFQA |
| 7 | KFGSTHA |
| 8 | FVNEIEA |

TABLE 1-continued

Six-amino acid sequences binding to SEQ ID NO: 1

| SEQ ID NO | SEQUENCE |
|---|---|
| 9 | GLHFKSA |
| 10 | GRVLHHA |
| 11 | QKNSEWA |
| 12 | HAYFTHA |
| 13 | WPKGAVA |

In a second preferred embodiment, the ligand is a protein or peptide having an amino acid sequence that binds to SEQ ID NO:2. The amino acid sequences set forth in Table 2 below (SEQ ID NOS:14-22) are examples of amino acid sequences that bind to SEQ ID NO: 2. Therefore, ligands having one or more of the sequences set forth in Table 2 are included in the ligands of the second preferred embodiment. The amino acid sequences set forth in Table 2 were identified in a 6-mer library screened for 6-mers that bind to SEQ ID NO:2. The library was constructed with an alanine (A) as a spacer between the resin and the combinatorial peptides of the library and is represented as the final A in the sequences. The amino acid lysine (K) is present eleven times, and the amino acid histidine (H) is present seven times, both which are above an average distribution of three. Therefore, six-mers containing the amino acid lysine (K) or histidine (H) are preferred. It will be understood by those skilled in the art that the ligands provided herein are not limited to those having the exemplary sequences set forth in Table 2.

TABLE 2

Six-amino acid sequences binding to SEQ ID NO: 2

| SEQ ID NO | SEQUENCE |
|---|---|
| 14 | RPWKKAA |
| 15 | PKHIWPA |
| 16 | HKLWGVA |
| 17 | GGYKPYA |
| 18 | ENVSQNA |
| 19 | HTYYNGA |
| 20 | KKKSDHA |
| 21 | HHLKGTA |
| 22 | KKHGVWA |

In a third preferred embodiment, the ligand is a protein or peptide having an amino acid sequence that binds to SEQ ID NO:3. The amino acid sequences set forth in Table 3 below (SEQ ID NOS:23-31) are examples of amino acid sequences that bind to SEQ ID NO: 3. Therefore, ligands having one or more of the sequences set forth in Table 3 are included in the ligands of the third preferred embodiment. The amino acid sequences set forth in Table 3 were identified in a 6-mer library screened for 6-mers that bind to SEQ ID NO: 3. The library was constructed with an alanine (A) as a spacer between the resin and the combinatorial peptides of the library and is represented as the final A in the sequences. In cases of sequence ambiguity in identification, one or more amino acids are given in a single position in the Table, for example, (A/G) as shown in SEQ ID NO: 29. The amino acid histidine (H) appears 10 times in these sequences, is found in six of the eight peptides, and is well above an average distribution of three. All peptides except SEQ ID NO: 23 have a net positive charge at pH 7. Therefore, six-mers containing the amino acid histidine (H) and peptides having a net positive charge at pH 7 are preferred. It will be understood by those skilled in the art that the ligands provided herein are not limited to those having the exemplary sequences set forth in Table 3.

TABLE 3

Six-amino acid sequences binding to SEQ ID NO: 3

| SEQ ID NO | SEQUENCE |
|---|---|
| 23 | DGTQAHA |
| 24 | APHRNNA |
| 25 | HHGHNIA |
| 26 | HTWHGQA |
| 27 | HVFVTWA |
| 28 | THHFYIA |
| 29 | KLGWG(A/G)A |
| 30 | GSKKKEA |

In a fourth preferred embodiment, the ligand is a protein or peptide having an amino acid sequence that binds to SEQ ID NO:4. The amino acid sequences set forth in Table 4 below (SEQ ID NOS:31-47) are examples of amino acid sequences that bind to SEQ ID NO:4. Therefore, ligands having one or more of the sequences set forth in Table 4 are included in the ligands of the fourth preferred embodiment. The amino acid sequences set forth in Table 4 were identified in a 6-mer library screened for 6-mers that bind to SEQ ID NO:4. The library was constructed with an alanine (A) as a spacer between the resin and the combinatorial peptides of the library and is represented as the final A in the sequences. It will be understood by those skilled in the art that the ligands provided herein are not limited to those having the exemplary sequences set forth in this Table 4. In cases of sequence ambiguity in identification, one or more amino acids are given in a single position, for example, (W/G) as shown in SEQ ID NO:33. The amino acid in the second position of SEQ ID NO:37 could not be positively identified. The sequence "LL" (two leucines) appears in SEQ ID NOS:31, 32, 41, 43 and 45 and its close analogs LI, VL, II (isoleucine or valine) appear in SEQ ID NOS:33, 36, 38, 40 and 44. LL does not appear in any other screens for prion-derived peptides or proteins. In addition, 15 of 17 peptides contain an aromatic amino acid, such as phenylalanine, tryptophan or tyrosine (F, W or Y). Seven peptide sequences are neutrally charged, but have a positive terminal amino group. Therefore, six-mers containing one or more leucine (L) or leucine analogs, such as isoleucine or valine (I or V) in sequence, preferably LL, LI, VL or II; six-mers containing an aromatic amino acid, such as phenylalanine, tryptophan or tyrosine (F, W or Y); and six-mers that are neutrally charged, but having a positive terminal amino group are preferred.

TABLE 4

Six-amino acid sequences binding to SEQ ID NO: 4

| SEQ ID NO | SEQUENCE |
|---|---|
| 31 | PLLVVWA |
| 32 | WLLVGGA |
| 33 | (W/G)QVLVYA |
| 34 | RRHQRQA |
| 35 | LPWTFGA |
| 36 | IFIIITA |
| 37 | P(X)IEPHA |
| 38 | EWGIIWA |
| 39 | GWYIYFA |
| 40 | TLILFHA |
| 41 | FLLSNHA |
| 42 | WQIRFFA |

TABLE 4-continued

| Six-amino acid sequences binding to SEQ ID NO: 4 | |
|---|---|
| SEQ ID NO | SEQUENCE |
| 43 | VLLVFEA |
| 44 | GWVLEIA |
| 45 | FLLIDTA |
| 46 | GFLFKFA |
| 47 | PWTIYIA |

Ligands that Bind to Hamster PrPc

In another embodiment, the ligand is a peptide that binds with specificity and selectivity to one or more forms of prion protein found in a particular species, such as human or another mammal, such as a hamster. Exemplary ligands that bind to prion protein (PrPc) having different amino acid sequence lengths, two-mer, three-mers, four-mers, five-mers and six-mers, preferably having a molecular weight of 6 kDa or less, are provided below.

Exemplary two-mer ligands that bind to native prion in hamsters (haPrPc) are set forth in SEQ ID NOS:48-50, which are listed in Table 5A. The ligand preferably contains the amino acid tryptophan (W). The preferred ligand is neutrally charged, but has a positive charged terminal amino acid group at pH 7. The preferred ligand is a two-mer containing the tryptophan (W). Substitution of naphthyl-alanine (na) for tryptophan also resulted in binding of PrP in these sequences. The library was synthesized directly onto the resin (a Toyopearl amino resin Tosoh Bioscience LLC, Monctgomerville, Pa.) without a spacer. SEQ ID NO:50 was found twice (2×) in the screens.

TABLE 5A

| Two-amino acid sequences binding to haPrPc | |
|---|---|
| SEQ ID NO | SEQUENCE |
| 48 | WH |
| 49 | WW |
| 50 | LW (2×) |

2 × denotes sequences found twice in the screen

Exemplary three-mer ligands that bind to prion in hamsters (haPrPc) are set forth in SEQ ID NOS:51-61, which are listed in Table 5B. An aromatic amino acid, F, W or Y appears in all peptides selected except SEQ ID NO:60. The amino acid A appears three times at the position closest to the resin and was used as a spacer between resin and peptide library in the some libraries. Neither R nor K is present, but E appears three times providing a negative charge to three of eight sequences.

TABLE 5B

| Three-amino acid sequences binding to haPrPc | |
|---|---|
| SEQ ID NO | SEQUENCE |
| 51 | WNA |
| 52 | EFW |
| 53 | LPW |
| 54 | YEY |
| 55 | WPA |
| 56 | FNQ |
| 57 | YHE |
| 58 | LFA |
| 59 | NHY |
| 60 | TLG |
| 61 | WVD |

Exemplary four-mer ligands that bind to prion in hamsters (haPrPc) are set forth in SEQ ID NOS:62-64, which are listed in Table 5C. The library was constructed with an alanine spacer between the resin and the combinatorial peptide and is present in the sequences below at the last position. An aromatic amino acid appears in the first position of all peptides selected. In addition, all peptides selected contain an acidic amino acid (D or E) at the third or fourth position. WXD appears once, where X is any amino acid.

TABLE 5C

| Four-amino acid sequences binding to haPrPc | |
|---|---|
| SEQ ID NO | SEQUENCE |
| 62 | YWDQA |
| 63 | YVHEA |
| 64 | WFDEA |

Exemplary five-mer ligands that bind to prion in hamsters (haPrPc) are set forth in SEQ ID NOS: 65-68, which are listed in Table 5D. An aromatic amino acid and an acidic amino acid appear in all peptides selected. D or E are present in position 4 or 5 of all ligands. The sequence WXD appears in SEQ ID NO:65, 67 and 68.

TABLE 5D

| Five-amino acid sequences binding to haPrPc | |
|---|---|
| SEQ ID NO | SEQUENCE |
| 65 | LQWYDA |
| 66 | YTHSEA |
| 67 | WIDYEA |
| 68 | VWIDAA |

Exemplary six-mer ligands that bind to prion in hamsters (haPrPc) are set forth in SEQ ID NOS:69-100, which are listed in Table 5E. The library was constructed with an alanine spacer between the resin and the combinatorial peptide and is present in the sequences below at the last position. An aromatic amino acid, F, W or Y appears in most (29 of 32) peptides selected as do D or E (29 of 32). In addition, 20 peptides have two aromatic amino acids in their sequence. The consensus sequence "WXD" appears in SEQ ID NOS: 75, 79, 83, 86 and 89. A sequence containing an (F/W/Y)X(D/E)(F/W/Y) SEQ ID NO:)) appears in SEQ ID NOS:71, 73, 77, 78, 91 and 95 and (F/W/Y)(D/E)X(F/W/Y) SEQ ID NO:)) appears in SEQ ID NOS:70, 72, 82, 91 and 95. Twenty four of 32 peptides have an aromatic amino acid plus an acid group in positions 1-3; 23 have a net negative charge in positions 4-6. Twenty peptides have both an aromatic amino acid plus an acid amino acid in positions 1-3 and are also net negative in positions 4-6.

TABLE 5E

| Six-amino acid sequences binding to haPrPc | |
|---|---|
| SEQ ID NO | SEQUENCE |
| 69 | WDEAEEA |
| 70 | YDSYDDA |
| 71 | NDFIDFA |
| 72 | YEPWGSA |
| 73 | EYGDWWA |
| 74 | WDYDQEA |
| 75 | DWGDPFA |
| 76 | DWPEVWA |
| 77 | FHDFSEA |
| 78 | DTFWDYA |

TABLE 5E-continued

Six-amino acid sequences binding to haPrPc

| SEQ ID NO | SEQUENCE |
|---|---|
| 79 | WNDLDNA |
| 80 | ASALVYA |
| 81 | LINAGGA |
| 82 | WESYVTA |
| 83 | WSDEGYA |
| 84 | YRWTGPA |
| 85 | YEDQWQA |
| 86 | EWADDNA |
| 87 | YEIDYGA |
| 88 | EFGYFDA |
| 89 | WGDEQDA |
| 90 | HEEDWAA |
| 91 | FEDFELA |
| 92 | TWGIDEA |
| 93 | WDPTDYA |
| 94 | NDKIHTA |
| 95 | FEDFFSA |
| 96 | YEWAEQA |
| 97 | THVYFLA |
| 98 | (S/T/W)XDFSDA |
| 99 | YRTPNEA |
| 100 | (G/L)RSETA |

Ligands that Bind to Hamster PrPc and Hamster PrPsc

In another embodiment, the ligand is a peptide that binds with specificity and selectively to two or more forms of prion. Ligands that bind to both (PrPc) and/or conformationally changed (PrPsc) prion protein are provided below. Exemplary three-mer ligands that bind to prion in hamsters (haPrPc) are set forth in SEQ ID NOS:101-115, which are listed in Table 6. An aromatic amino acid appears in most (15 of 18) peptides selected as do D or E (15 of 18). In addition, seven peptides have two aromatic structures and an acidic amino acid. The sequence WXD appears in SEQ ID NOS:105 and 115. Structures selected to bind preferentially PrPsc over PrPc are SEQ ID NO:111 and SEQ ID NO:114, both having R at position 3. SEQ ID NO:101-115 were identified in a 3-mer library to bind haPrPc and/or PrPsc from homogenates of scrapie-infected brain either alone (*), or mixed with normal hamster brain.

TABLE 6

Three-amino acid sequences binding to haPrPc and haPrPsc

| SEQ ID NO | Sequence | Bead color (red shows strong PrPc binding) | Light signal after denaturation (strong shows strong PrPc and/or PrPsc binding) |
|---|---|---|---|
| 52 | EFW* | Bright pink | Strong |
| 54 | YEY | Pink | |
| 101 | IHN | Light pink | |
| 102 | WEY | Bright pink | |
| 103 | DYW | Pink | |
| 104 | WDW | Pink | |
| 105 | WQD | Pink | |
| 106 | YFE | Pink | |
| 106 | YFE* | Red | Strong |
| 107 | NYE | Pink | |
| 108 | SYA | Light pink | None |
| 109 | WDL | Bright pink | Strong |
| 110 | WLE | Bright pink | Weak |
| 111 | VQR | Bright pink | Very strong |
| 112 | YID* | Bright pink | Strong |
| 113 | RWD* | Bright pink | Strong |
| 114 | DVR* | White | Strong |
| 115 | WSD* | Red | Strong |

Ligands that Bind to Human PrPc

Ligands that bind to (huPrPc) prion protein are provided below. Exemplary three-mer ligands that bind to prion in humans (haPrPc) are set forth in SEQ ID NOS:116-139, which are listed in Tables 7A and B. Of the trimer sequences (Table 7A) W/YXD appears in four of the six trimer sequences and five of the six have a hydrophobic and an acidic amino acid residue.

TABLE 7A

Three-amino acid sequences binding to huPrPc

| SEQ ID NO | SEQUENCE |
|---|---|
| 116 | HWD |
| 117 | WQD |
| 118 | WDD |
| 119 | WED |
| 120 | ITN |
| 121 | YED |

The six-mer library was constructed with an alanine spacer between the resin and the combinatorial peptide and is present in the sequences below at the last position (Table 7B). Amino acids F, W or Y appear in 13 of 18 6-mer peptides, and D or E in 17 of 18 peptides. Six peptides have an aromatic and an acid amino acid in positions 1-3 and are also net negative in positions 4-6. In addition, five peptides have two aromatic structures and an acid amino acid. W×D is present in SEQ ID NO:124 and (F/W/Y)x(D/E)(F/W/Y) (SEQ ID NO:223) is present in SEQ ID NOS:124 and 133. Excluding the N-terminal amino charge the majority of sequences are net negative and only SEQ ID NO:139 carries a partial net positive at neutral pH. SEQ ID. NOS: 116-121 were identified in a 3-mer library to bind huPrPc from normal human brain homogenates. SEQ ID NOS:122-139 were identified in a 6-mer library to bind either human platelet poor plasma or platelet rich plasma (*) derived huPrPc.

TABLE 7B

Six-amino acid sequences binding to huPrPc

| SEQ ID NO | SEQUENCE |
|---|---|
| 122 | RVADEEA |
| 123 | EYYVDAA |
| 124 | WQDFNLA |
| 125 | YDNPIDA |
| 126 | YFNEHEA |
| 127 | EWGADGA |
| 128 | DVIYSHA |
| 129 | WHILEEA* |
| 130 | NPHENFA* |
| 131 | HEDNGGA |
| 132 | SDSEGPA |
| 133 | EFQEFTA |
| 134 | QEGDEIA |
| 135 | DIYAETA |
| 136 | DRVRETA |
| 137 | FEEPQWA* |
| 138 | FEGEEFA* |
| 139 | (T/L)FNIHA* |

*bound platelet rich plasma derived huPrPc

Ligands the Bind to Human Recombinant PrP

Ligands that bind to recombinant (PrPr) prion protein are provided below. Exemplary three-mer ligands that bind to recombinant prion in humans (huPrPr) are set forth in SEQ ID NOS:54, 105, 140-153, which are listed in Table 8. Amino Acids W, F or Y appear in all 16 peptides selected from D or E in 13 of 16 peptides. The consensus sequence WXD appears in SEQ ID NOS:105, 143 and 145. Some peptides have been previously identified to bind PrPc and SEQ ID NOS:149 and 153 were identified twice in this screen. SEQ ID NOS:54 105, 140-153, were identified in a 3-mer library to bind huPrPr (Prionics AG, Switzerland, Cat.) #03-0404) diluted into (*) 0.5% sarcosyl or (**) PBS. In Table 8, 2.5 mg of dry weight of resin from a combinatorial library per column was exposed to 0.5 μg/ml of PrPr diluted into 0.5% sarcosyl (*) or into phosphate-buffered saline (**) containing 1% BSA. Sequences found twice in the screen are denoted 2×.

TABLE 8

Three-amino acid sequences binding to huPrPr

| SEQ ID NO | SEQUENCE |
|---|---|
| 54 | YEY** |
| 105 | WQD* and **(2×) |
| 140 | YDW* |
| 141 | NYT* |
| 142 | SYT* |
| 143 | WAD* |
| 144 | QWG* |
| 145 | WGD* |
| 146 | EYF* |
| 147 | WEH* |
| 148 | LYD* |
| 149 | DYY* *(2×) |
| 150 | FYE** |
| 151 | EYY** |
| 152 | YDY** |
| 153 | WDH** (2×) |

*Human PrPr diluted into 0.5% sarcosyl
**Human PrPr diluted into PBS
2 × denotes sequences found twice in the screen Six-Mer Ligands that Bind to Human PrPc, Human PrPsc or Both Six-mer ligands that bind to (PrPc) prion protein, conformationally changed (PrPsc) prion protein, or both are provided in TABLE 9A. The six-mer library was constructed with an alanine spacer between the resin and the combinatorial peptide and is present in the sequences below at the last position The ligands may preferentially to huPrPsc. Exemplary ligands are set forth in SEQ ID NOS:154-173, which are listed in Table 9A. All ligands except SEQ ID NO:156 contained an aromatic amino acid and 15 of 20 contained an acidic amino acid. Those with greater specificity for huPrPsc over PrPc are SEQ ID NO:154, 155 and 156. Detection of ligands with increased specificity for PrPsc in a brain homogenate derived from a sporadic CJD patient was obtained through selective proteolysis of PrPc prior to transfer of protein from beads to membrane. This library included the unnatural aromatic amino acid 2-naphthyl-alanine (na).

TABLE 9A

Six-amino acid sequences that bind to huPrPc, huPrPsc or both

| SEQ IN NO | Sequence |
|---|---|
| 154* | RES(na)NVA |
| 155* | ES(na)PRQA |
| 156* | VARENIA |
| 157* | RWEREDA |
| 158** | EWWETV |
| 159** | SVYQLDA |
| 160** | (na)HEFYGA |
| 161** | HE(na)(na)LVA |
| 162** | A(na)VPV(na)A |
| 163** | YFDYWLA |
| 164** | FE(na)HRQA |
| 165** | WRHEPAA |

TABLE 9A-continued

Six-amino acid sequences that bind to huPrPc, huPrPsc or both

| SEQ IN NO | Sequence |
|---|---|
| 166*** | SS(na)KKDA |
| 167*** | R(na)DKEAA |
| 168**** | (na)HEIFPA |
| 169**** | KWYHHRA |
| 170**** | HWWPHNA |
| 171**** | HWQVFYA |
| 172**** | FHE(na)EIA |
| 173**** | HADF(na)QA |

*0.5% sporadic CJD (huPrPsc) brain homogenate without PK treatment
**5% huPrPsc brain homogenate without PK treatment
***0.5% huPrPsc brain homogenate with PK treatment, but no color development
****5% huPrPsc brain homogenate with PK treatment, but with no color development
na denotes 2-naphtyle-alanine Ligands that Bind to Human PrPsc Ligands that bind to conformationally changed prion protein (PrPsc) are provided below. The six-mer libraries were constructed with an alanine spacer between the resin and the combinatorial peptide and are included in the sequences below at the last position. Exemplary ligands are set forth in SEQ ID NOS:174-194, which are listed in Table 9B. SEQ ID NOS:188, 189, 190, and 191 all showed highest differentiation of signal (white color and strong light signal). SEQ ID NOS:174-194 were identified in a 6-mer-library to bind huPrPsc from sporadic CJD brain homogenate spiked into human plasma. Beads with ligands with highest specificity for PrPsc were white on staining for PrPc, but produced a strong chemiluminescent signal following denaturation.

TABLE 9B

Six-amino acid sequences that bind to huPrPsc

| SEQ ID NO | Sequence |
|---|---|
| 174* | ALHFETA |
| 175* | DDPTGFA |
| 176* | VAPGLGA |
| 177* | IFRLIEA |
| 178* | GLERPEA |
| 179* | IVVRLWA |
| 180* | WHNPHYA |
| 181* | LIYKSDA |
| 182** | EKPIFNA |
| 183** | HWSEPAA |
| 184** | GHNWKEA |
| 185** | YWHHDDA |
| 186** | GYPKENA |
| 187** | PVYWLYA |
| 188*** | FGEHTPA |
| 189*** | FQGTREA |
| 190*** | TGTNRYA |
| 191*** | KWATRYA |
| 192*** | NSTKFDA |
| 193*** | LIYKEEA |
| 194*** | EHATYRA |

*100-300 μm beads screened with sporadic CJD brain derived brain homogenate (huPrPsc) with PK treatment
**100-300 μm beads screened with huPrPsc without PK treatment
***65 μm beads screened with huPrPsc without PK treatment Three-Mer Ligands that Bind to Human PrPc, Human PrPsc or Both Three-mer ligands that bind to (huPrPc) prion protein, conformationally changed prion protein (PrPsc), or both, are provided below. The ligands may bind preferentially to huPrPsc. Exemplary ligands are set forth in SEQ ID NOS: 195-212, which are listed in Table 9C. In this screen, the sporadic CJD brain homogenate was diluted in CPD and was used as the source of huPrPsc. HYD was discovered 3 times in this screen. Red beads signified the binding of PrPc; 8 of 13 sequences contained H. Amino Acids F, W or Y were found in all 13, and R or K appeared only once. Three of five beads that preferentially bound PrPsc (strong signal) relative to PrPc (white bead) contained K or R. WXD appeared in SEQ ID NOS:200 and 208. SEQ ID NOS:195-212 were identified in a 3-mer library to bind huPrPc and/or huPrPsc treated with PK.

TABLE 9C

Three-amino acid sequences that bind to huPrPc, huPrPsc, or both PK-resistant

| SEQ ID NO | Sequence |
|---|---|
| 195* | HND |
| 196* | HER |
| 197* | HGD |
| 198* | HSD |
| 199* | HFD |
| 200**** | WND |
| 201**** | YEH |
| 202**** | HWD |
| 203**** | YHD |
| 204**** | YDW |
| 205**** | WDY |
| 206** | HYD (3×) |
| 207** | HWD |
| 208** | WTD |
| 209*** | FPK |
| 210*** | HWK |
| 211*** | WEE |
| 212*** | LLR |

*0.5% huPrPsc in 0.05% sarcosyl plus PK treatment

**1.0% huPrPsc in 0.1% sarcosyl without PK treatment

***1.0% huPrPsc in 0.1% sarcosyl with PK treatment

****beads were selected from the gel before transfer; for SEQ ID NOS: 204 and 205, beads incubated in 0.1% huPrPsc in 0.01% sarcosyl with PK treatment were selected following washing and taken directly from the gel Three-Mer Ligands that Bind to Human PrPc, Human PrPsc or Both Three-mer ligands that bind to (PrPc) prion protein, conformationally changed (PrPsc) prion protein, or both, are provided below. The ligands may preferentially bind to huPrPsc. Exemplary ligands are set forth in SEQ ID NOS: 147, 152, 206, 213, and 214, which are listed in Table 9D. These sequences were identified in a 3-mer library to bind huPrPsc and/or huPrPc from sporadic CJD brain homogenate diluted into (*) CPD buffer or (**) PBS.

TABLE 9D

Three-amino acid sequences that bind to huPrPc, huPrPsc, or both

| SEQ ID NO | Sequence |
|---|---|
| 147* | WEH |
| 152* | YDY |
| 206* | HYD |
| 213** | SYF |
| 214** | EYY |

*sporadic CJD brain homogerate diluted into CPD buffer

**sporadic CJD brain homogenate diluted into PBS

Synthesis of Ligands

The ligands described herein may be produced by chemical synthesis. A variety of protein synthesis methods are common in the art, including synthesis using a peptide synthesizer. See, for example, *Peptide Chemistry, A Practical Textbook*, Bodasnsky, Ed. Springer-Verlag, 1988; Merrifield, Science 232: 241-247 (1986). Preferably, the peptides are synthesized, purified and then coupled to a resin or a membrane used for screening. Alternatively, the peptides are synthesized directly on a resin, and the resin-bound peptides are then purified.

The peptides are purified so that they are substantially free of chemical precursors or other chemicals used in standard peptide purification techniques. The language "substantially free of chemical precursors or other chemicals" includes preparations of a peptide in which the peptide is separated from chemical precursors or other chemicals that are involved in the synthesis of the peptide.

Chemical synthesis of peptides facilitates the incorporation of modified or unnatural amino acids, including D-amino acids and other small organic molecules. Replacement of one or more L-amino acids in a peptide with the corresponding D-amino acid isoform can be used to increase the resistance of the peptides to enzymatic hydrolysis, and to enhance one or more properties of the active peptides, such as prion or ligand binding. The prion peptide and the peptide ligands described herein can be polymers of L- or D-amino acids, or a combination of both. Also included are ligands in which analogs of the peptide ligands described herein are present in non-peptidyl linkages.

For example, in various embodiments, the peptide ligands are D-retro-inverso isomer peptides. The term "retro-inverso isomer" refers to an isomer of a linear peptide in which the direction of the sequence is reversed and the chiralty of each amino acid residue is inverted. See, for example, Jameson et al., *Nature,* 368: 744-746 (1994). The net result of combining D-enantiomers and reverse synthesis is that the positions of carbonyl and amino groups in each amide bond are exchanged, while the position of the side-chain groups at each α-carbon is preserved. Unless stated otherwise, it is presumed that any given L-amino acid sequence of the invention may be made into a D-retro-inverso isomer peptide.

Additional covalent cross-links can be introduced into the peptide sequence to constrain the structure of the peptide backbone. This strategy can be used to develop peptide analogs with increased potency, selectivity and stability. Macrocyclization is often accomplished by forming an amide bond between peptide N- and C-termini, between a side chain and the N- or C-terminus, for example, with K3Fe(CN)6 at pH 8.5 (Samson et al., *Endocrinology,* 137: 5182-5185 (1996)) or between two amino acid side chains. See, for example, DeGrado, *Adv. Protein Chem.,* 39:51-124 (1988).

A number of other methods can also introduce conformational constraints into peptide sequences in order to improve their potency, stability and selectivity. These include the use of C α-methylaminoacids (see, for example, Rose et al., Adv. Protein Chem., 37:1-109 (1985)) or N α-methylamino acids (see, for example, Aubry et al., *Int. J. Pept. Protein Res.,* 18:195-202 (1981)).

If desired, two or more peptide ligands can be present in multiple copies. Identical copies of one or more peptides can be present (for example, homodimers, homotrimers, etc), or multiple copies of peptides varying in sequence can be present (for example, heterodimers, heterotrimers, etc.).

In an alternative, the ligands are synthesized using recombinant nucleic acid methodology. Generally, this involves creating a nucleic acid sequence that encodes the ligands, placing the nucleic acid in an expression cassette under the control of a particular promoter, expressing the protein in a host, isolating the expressed protein and, if required, renaturing the protein. Techniques sufficient to guide one of skill through such procedures are known to those skilled in the art.

Once expressed, recombinant ligands can be purified according to standard procedures, including ammonium sulfate precipitation, affinity columns, column chromatography, gel electrophoresis and the like. Substantially pure compositions of about 50 to 95% homogeneity are preferred, and approximately 80 to 95% or greater homogeneity is most preferred for use as therapeutic agents.

Optionally, the ligands are combined into mosaic proteins. Typically, 2 to 20 of the ligands are fused into a single polypeptide by recombinant or synthetic techniques.

In recombinant procedures, mosaic proteins are made by ligating synthetic or recombinant nucleic acids which encode immunogenic peptides. These nucleic acids can be ligated enzymatically (for example, using a DNA Ligase enzyme) or synthetically. Alternatively, a single nucleic acid can be synthesized which encodes multiple ligand peptides. In either case, the resulting nucleic acid encodes multiple ligands, all in the same reading frame. Thus, the translated polypeptide comprises prion-binding ligands.

Where the ligands are made by automated chemical synthetic procedures, concatamers of peptides can be coupled directly. This is performed chemically by joining peptides using standard chemical methods. Alternatively, a polypeptide can be synthetically produced which encodes multiple ligand peptides.

Ligand Identification

In addition to the ligands set forth above in the tables, additional ligands can be identified as follows. Peptide libraries are synthesized and screened for the ability to bind to prion analytes. The ligands can be of any length. However, lengths from two to six amino acids are preferred. The synthetic peptides are immobilized on beads, and the beads packed into a chromatography column. Prion analyte is then passed through the column and bound analyte is detected using conventional methods such as by a labelled antibody specific for prion protein. Beads to which the analyte has bound are identified as being suitable ligands.

Use of Ligands to Remove Prions

Ligands that bind prions or fragments of prions are useful for a variety of analytical, preparative, and diagnostic applications. Prion-binding ligands may be immobilized on a support such as a bead or membrane, and used to bind and remove prion from a sample. The solid phase to which the ligands are bound is allowed to contact the sample, such as a biological fluid, under conditions sufficient to cause formation of a prion-ligand composite, and prion protein in the sample binds to the ligand. The solid phase is then separated from the sample, thereby removing the prion protein bound to the ligand, which is attached to the solid phase, from the sample. For example, resins and membranes for removal of contaminants are well known in the art such as those described in U.S. Pat. No. 5,834,318 to Baumbach et al. and PCT/US01/11150.

Examples of biological samples include, but are not limited to, blood, blood-derived compositions or serum. Additional biological samples include cerebrospinal fluid, urine, saliva, milk, ductal fluid, tears or semen. Other samples may contain collagen, brain and gland extracts.

Many methods for immobilizing molecules to a variety of solid surfaces are known in the art. For instance, the solid surface may be a membrane (for example, nitrocellulose), a microtiter dish (for example, PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, polyacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (for example, gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system. In addition, the peptide may be incorporated during polymerization of the solid surface.

In preparing the surface, a plurality of different materials may be employed, for example, laminates, to obtain various properties. For example, protein coatings, such as gelatin can be used to avoid non specific binding, simplify covalent conjugation, and enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Prion proteins may also be separated from other proteins in a sample by using affinity chromatography. Ligands according to the invention can be attached to a solid support, such as a resin or a membrane, and used to bind and remove the prion from solution. In this instance, the ligand may be coupled to a solid support, for example, an inert support such as a membrane or a resin, and the prion protein binds to the immobilized agent. The immobilized agent/prion may be detected by means of antibodies. If desired, one or more of the sequences obtained from the initial screening may be immobilized on a resin, such a polymethacrylate or agarose. Other types of resin that may be used include, for example, sepharose, cross-linked agarose, composite cross-linked polysaccharides, celite, PVDF, acrylate, polystyrene and cellulose. Membranes, such as, nylon and cellulose, may also be used. The resin may be a polymethacrylate resin.

Use of Ligands to Detect Prions

The ligands described herein are also useful in a method of detecting the presence of or quantifying a prion protein in a biological sample. A biological sample such as, but not limited to, those listed above, is contacted with a ligand under conditions sufficient to cause formation of a complex between the prion protein and the ligand. The complex is then detected by conventional methods, thereby detecting the presence of the prion in the biological sample.

The complex is detected by labelling the ligand, combining the labelled ligand with the sample, and detecting labelled ligand-prion complex. The ligand is labelled during ligand production, such as during peptide synthesis, or a label is conjugated to the ligand by joining it to the ligand, either covalently or non-covalently. Alternatively, a binding molecule specific for the ligand, such as an antibody, is labelled and the complex is detected indirectly. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Detection may proceed by any known method, such as immunoblotting, Western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size or charge or both. The particular label or detectable group used in the assay is not a critical aspect of the invention. The detectable group can be any material having a detectable physical or chemical property. Such detectable labels have been well-developed and, in general, any label useful in such methods can be applied to the present method. Thus, a label is any composition detectable by spectroscopic, photochemical, biochemical, immunochemical, electrical, optical or chemical means. Useful labels in the present invention include fluorescent dyes (for example, fluorescein isothiocyanate, Texas red, rhodamine, and the like), radiolabels (for example, $^3H$, $^{125}I$, $^{35}S$, $^{14}C$, or $^{32}P$), enzymes (for example, LacZ, CAT, horse radish peroxidase, alkaline phosphatase and others, commonly used as detectable enzymes, either in an EIA or in an ELISA), and colorimetric labels such as colloidal gold or colored glass or plastic (for example, polystyrene, polypropylene, latex, etc.) beads. The label may be coupled directly or indirectly to the desired component of the assay according to methods well known in the art. As indicated above, a wide variety of labels may be used, with the choice of a label depending on the sensitivity required, ease of conjugation of the compound, stability requirements, available instrumentation, and disposal provisions.

Non-radioactive labels are often attached by indirect means. Generally, a ligand molecule (for example, biotin) is covalently bound to the molecule. The ligand then binds to an anti-ligand (for example, streptavidin) molecule, which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, for example, luminol.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, for example, by microscopy, visual inspection, via photographic film, by the use of electronic detectors such as charge coupled devices (CCDs) or photomultipliers and the like. Similarly, enzymatic labels are detected by providing appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

The ligands of the invention can also be used to detect targets extracted into solution from a solid material. For example, a solid sample can be extracted with an aqueous, an organic solvent or a critical fluid and the resultant supernatant can be contacted with the ligand. Examples of solid samples include animal-derived products, particularly those that have been exposed to agents that transmit prions, for example, bone meal derived from bovine sources. Ligands in some embodiments can be used to detect the presence of prion protein in soil. Other solid samples include brain tissue, corneal tissue, fecal matter, bone meal, beef by-products, sheep, sheep by-products, deer and elk, deer and elk by-products, and other animals and animal derived products.

Alternatively, the prion-ligand complexes may be treated with PK. PrPc is highly sensitive to PK, while PrPsc is partially digested to form PrPres. The PrPres molecule itself is highly resistant to proteolysis. Thus, PK treatment will digest PrPc, and will convert PK sensitive PrPsc to PrPres. Following removal of PK, the PrPres can be denatured and detected by antibodies, such as 3F4.

In another embodiment, ligands according to the invention may be used for the selective concentration of PrPsc over PrPc.

Use of Ligands to Quantify Prions

A ligand-prion complex, or alternatively, an antibody to the ligand or ligand-prion complex, can be detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like.

Reduction of Non-Specific Binding

One of skill in the art will appreciate that it is often desirable to reduce non-specific binding in assays and during analyte removal from a sample. Where the assay involves a ligand or other capture agent immobilized on a solid substrate, it is desirable to minimize the amount of non-specific binding to the solid substrate. Means of reducing such non-specific binding are well known to those of skill in the art. Typically, this involves coating the substrate with a proteinaceous composition. In particular, protein compositions such as bovine and human serum albumin (BSA), nonfat powdered milk, and gelatin are widely used.

Other Assay Formats

Western blot analysis can also be used to detect and quantify the presence of prion protein in a sample. The technique generally involves separating sample products by gel electrophoresis on the basis of molecular weight in the presence of SDS, transferring the separated proteins to a suitable solid support (such as a nitrocellulose filter, a nylon filter, or derivatized nylon filter), and incubating the bound sample with the ligands described herein. The ligands specifically bind to a prion peptide fixed on the solid support. These ligands are directly labeled or, alternatively, they may be subsequently detected using labeled antibodies that specifically bind to the ligand.

Other assay formats include liposome immunoassays (LIAs), which use liposomes designed to bind specific molecules (for example, ligands) and release encapsulated reagents or markers. The released chemicals are then detected according to standard techniques.

Pharmaceutical Compositions

The ligands described herein are useful in therapeutic and prophylactic applications for the treatment of TSEs caused by infection of a mammal with prion organisms. For instance, in one embodiment, a method of treating TSEs in a mammal is provided by administering to the mammal an effective amount of a pharmaceutical composition containing a pharmaceutically acceptable carrier and a synthetic or isolated ligand as described herein. The ligand may prevent polymerization of PrPsc through inhibition of the binding of PrPsc to PrPsc. In addition it may prevent inhibit binding of PrPsc to PrPc so decreasing PrPsc mediated conversion of PrPc to PrPsc thereby delaying the onset of clinical symptoms. Moreover, the ligands themselves may be modified by the addition of a reactive agent to target that molecule to the site of PrPsc accumulation. Such compositions are suitable for use in a variety of drug delivery systems.

Diseases to be treated in accordance with the method include, but are not limited to, BSE, transmissible mink encephalopathy, feline spongiform encephalopathy, CWD, CJD, GSS, fatal insomnia, and vCJD.

The pharmaceutical compositions are intended for parenteral, topical, oral or local administration. Preferably, the pharmaceutical compositions are administered parenterally, for example, intravenously, subcutaneously, intradermally, intranasally or intramuscularly. Thus, the invention provides compositions for administration that comprise a solution of the agents described above dissolved or suspended in an acceptable carrier, preferably an aqueous carrier. A variety of aqueous carriers may be used, for example, water, buffered water, 0.4% saline, 0.3% glycine, hyaluronic acid, fibrin sealant and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally approximately 1% to 95% of active ingredient and more preferably at a concentration of approximately 25% to 75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, for example, lecithin for intranasal delivery.

The amount administered will vary depending upon what is being administered, the state of the mammal receiving treatment and the manner of administration. In therapeutic applications, compositions are administered to a mammal already suffering from prion infection in an amount sufficient to inhibit spread of the prions, or at least partially arrest the symptoms of the disease and its complications. An amount adequate to accomplish this is defined as "therapeutically effective dose." Amounts effective for this use will depend on the severity of the disease, the particular composition, and the weight and general state of the recipient. Generally, the dose will be in the range of about 1 mg to about 5 mg per day, preferably about 100 mg per day, for an approximately 70 kg patient.

In addition, DNA or RNA encoding the ligands may be introduced into mammals to obtain the desired therapeutic response to the ligand which the nucleic acid encodes.

The invention will be described in greater detail by way of specific examples. The following examples are offered for illustrative purposes, and are intended neither to limit nor define the invention in any manner.

Example 1

Identification of Prion-Binding Ligands

The prion-binding ligands described in the Tables set forth herein were identified as follows.

Peptide Library Synthesis

The peptides and peptide libraries useful for the identification of the prion-binding ligands described herein were synthesized by either Peptides International (Louisville, Ky.) or Commonwealth Biotechnologies (Richmond, Va.) directly on Toyopearl amino resin (TosoBioSep, Montgomeryville, Pa.) using standard Fmoc chemistry based on methods described by Buettner, et al. 1996. Peptide densities achieved with the above scheme were typically in the range of 0.1-0.5 mmole/gram resin. Libraries comprising 1, 2, 3, 4, 5 and 6 amino acids were synthesized. The 4, 5 and 6 amino acid libraries were synthesized on amino Toyopearl and contained a mixture of tBoc and Fmoc alanine as a spacer between the amino acid and the amino group on the resin. The peptides were synthesized from the Fmoc alanine and the tBoc was acetylated. The presence of "A" was often found in the first position of this library, along with the amino terminal amino acid of the ligand. This was probably due to partial deacylation during peptide synthesis, deprotection and/or Edman degradation during sequencing.

In some embodiments, individual beads, each carrying multiple copies of a unique ligand, are immobilized in agarose after previous contact with a solution containing PrP. Since a large number of ligands can be synthesized onto the surface of beads, it is possible to produce enormous numbers of beads each of which theoretically bears a unique ligand. These ligands are screened using the described methods for initial leads. Once a lead has been identified, additional ligands (sub-libraries) are synthesized based on the lead ligand. Screening of these sub-libraries may lead to additional ligands with improved characteristics. Through a process of iteration of synthesis and screening it is possible to identify preferred ligands.

Peptide Library Binding Screening

Varying amounts of beads (5-500 mg of dry beads) from a library were placed into a Bio-Spin® disposable chromatography column (Bio-Rad Laboratories, Cat.#732-6008), and were washed with 20 column volumes (CV) of 20% MeOH in $H_2O$ to remove possible impurities and organic solvents used in peptide synthesis. The beads were then washed and equilibrated using 20 CV of 1×TBS, pH 7.6 (1×TBS was prepared by 10-fold dilution of 10×TBS, BioSource International, Camarillo, Calif. Cat. #616US-000). The flow was then stopped and the beads were suspended in 1 ml of fresh 1×TBS and allowed to swell for an additional 15 minutes. TBS was drained by gravity and the column was closed. To prevent non-specific binding of test material to the resin 1 mL of Blocker™ Casein in TBS (Pierce, Rockford, Ill. Cat #37532) solution with added 0.5% BSA (Sigma, Cat#A-7030) was applied to the beads. After covering both ends of the column, blocking was performed overnight at 4° C., under gentle agitation. The blocking solution was drained, and 1 ml of test material containing PrPr, PrPc and/or PrPsc was added to the resin. The column was tightly closed at both ends placed in horizontal position, and gently agitated at room temperature, for three hours. The PrP-containing material was drained out and beads were washed under gravity, driven with 10 mL of TBS containing 0.05% Tween 20 followed by 10 mL of TBS.

Detection of Bound PrPc

Detection of normal PrPc was performed using mouse monoclonal antibody 3F4 (Signet, Dedham, Mass.) diluted 1:8,000 in TBS containing 1% casein. The monoclonal antibody binds haPrPc, huPrPc and huPrPr, but has extremely little, or no affinity for haPrPsc or huPrPsc; however, it does bind denatured haPrPsc and huPrPsc. One milliliter of diluted 3F4 antibody was added to beads from a combinatorial library previously exposed to material containing PrPc. The beads were gently agitated with 3F4 at room temperature, for one hour. Solution containing non-bound antibody was drained out and the beads were washed with 10 mL of TBS and 10 mL of TBS containing 0.1% Tween 20. The beads were then incubated in 1 mL of alkaline phosphatase labeled Goat Anti-Mouse IgG (γ) (KPL, Gaithersburg, Md. Cat #741806.) diluted 1:2,000 in 0.5% casein/0.5% BSA in TBS. Incubation was carried out with gentle agitation for 1 hour at room temperature. Solution containing non-bound secondary antibody was drained out and the beads were washed with 10 mL of TBS and 10 mL of T-TBS. Next, 1 mL of ImmunoPure Fast solution, a substrate for alkaline phosphatase (Pierce, Rockford, Ill., cat. #34034) was prepared as described by the manufacturer and applied to the beads. Incubation proceeded at room temperature for about 15 minutes or until beads started turning light pink, and few dark red beads appeared. The substrate solution was drained and the beads washed with 10 mL of TBS.

Detection of PrP-Binding Beads Embedded in Agarose

Identification of PrP-binding beads embedded in agarose was performed as follows. First, the base layer of agarose was prepared by covering the surface of a 49 $cm^2$ tray with 9 ml of 1% agarose (Life Technologies, Grand Island, Nebr., cat. #15510-027) dissolved in water, which was previously melted and cooled to about 60° C. The agarose was allowed to solidify. Beads were contacted with test material containing prion protein and washed in TBS as described above. Next, the concentration of beads was adjusted according to the desired concentration of the beads in the gel. A good spread of the beads was found at 1.9 mg dry weight equivalent/ml. 90 µl of bead slurry was added to 800 µl of 0.5% low melting point agarose (BioWhittaker, Rockland, Me. cat. #50111) that had been dissolved in water, melted and cooled to about 40° C. The mixture was gently vortexed very briefly and poured over the surface of the base layer. An aliquot of PrP containing material was placed directly into the gel at its corner and served as a positive control for the next procedures. The gel was allowed to solidify at 4° C.

Chemiluminescent Detection of PrP-Binding Beads Embedded in Agarose

After embedding the beads in the gel, a solution of CDP-Star (Applied Biosystems, Bedford, Mass. cat. #MS100R) was added to cover the surface of gels which were then incubated for 5 minutes as described in the manufacturer's instructions protocol. Gels were drained of surplus substrate solution, then placed on a transparency, sealed in a plastic bag and exposed to autoradiography film for 30 minutes. The films identified the location of PrPc or PrPr by spots aligning with red beads in the gel. These films were subsequently used to align films additional films obtained after denaturing transfer of proteins to a nitrocellulose membrane.

Protocol for Protein Transfer from the Embedded Beads to Nitrocellulose Membrane.

This transfer methodology elutes proteins from beads and transfers them through capillary action onto nitrocellulose or PVDF membrane. A piece of 3 MM filter paper acts to wick transfer buffer (which can be any buffer that is suited to the particular needs of the experiment) from a tank through the gel. The 3 MM wick is pre-wetted with transfer buffer and placed on a surface with the ends of the paper immersed in the buffer tank. The gel is placed, soft agar side up, on the wet 3 MM, making sure that there are no bubbles between the paper and the gel. A piece of membrane (ECL-standard nitrocellulose Hybond Amersham, Germany, cat. #RPN303D) cut to the size of the gel is wetted in the transfer buffer and placed on top of the gel. A pipette is rolled over the membrane to eliminate bubbles. Two pieces of pre-wetted 3 MM paper are then placed on the membrane and rolled with a pipette to remove air bubbles. A stack of dry paper towels or other absorbent paper is placed on top, and weighted with 300 g weight. Transfer can proceed as long as necessary.

Protocol for Chemiluminescence (ECL) Detection

The membranes are removed from the top of the gels, rinsed, and placed in plastic containers with 10 mL of 5% (w/v) dried, fat-free milk Giant Fod Inc., Landover, Md. in TBS plus Tween (T-TBS). The membranes are incubated with the milk with gentle agitation for up to 16 hours at 4° C., or two hours at room temperature, to prevent non-specific binding of antibodies to the membranes. After blocking with milk, the membranes are incubated with 10 ml of a 1:8,000 dilution of primary antibody, 3F4, in 5% milk in TBS plus Tween (T-TBS). Incubation is allowed to continue with gentle agitation for 1.5 hours at room temperature (20-25° C.). The primary antibody solution is then discarded and the membranes rinsed twice with T-TBS, then washed for 15 minutes in T-TBS, then twice for five minutes in fresh T-TBS. All washes are performed with gentle agitation. Each membrane is then incubated for 1.5 hours at room temperature with gentle agitation with 10 ml of a 1:10,000 dilution of horse radish peroxidase (HRP) labeled secondary antibody (KPL, Gaithersburg, Md.) in 5% milk in T-TBS. The secondary antibody solution is then discarded and the membranes rinsed and washed as above. Some experiments used alkaline phosphatase labeled secondary antibody for detection of primary antibody.

Chemiluminescent detection is accomplished by preparing "Chemiluminescent Substrate" (Supersignal, Pierce Rockford Ill. cat #34080) according to the manufacturer's instructions. Ten milliliters of the mixture is added to each membrane, protein side up. The substrate is gently swirled manually for five minutes, and the substrate-saturated membranes removed and placed on 3 MM filter paper to drain quickly, then wrapped in Sheet Protector (Boise Cascade Office Products, #L2A9113-NG). The protein side of the membranes is exposed to autoradiography film for various periods of time and the films developed.

Detection of Trimer-Binders Specific for PrPsc from Scrapie Hamster Brain

Different biochemical properties between PrPc and PrPsc and the binding of antibodies, that is, 3F4, were exploited to screen for ligands that selectively bind to PrPsc. The monoclonal antibody 3F4 binds to denatured PrPsc with considerably higher affinity than to non-denatured PrPsc. (Safir, J. et al. Eight Prion Strains Have PrPsc Molecules With Different Conformations. 1998. *Nature Medicine* 4:1157-1165)

Ten percent (w/v) homogenates of uninfected and scrapie-infected hamster brains were prepared in PBS and stored frozen at −80° C. (courtesy of Dr. Robert Rohwer, Va. Medical Center, Baltimore). Prior to use they were thawed on wet ice, and 1.2 ml (uninfected) and 0.5 ml (infected) homogenates, were solubilized in the presence of sarcosyl at a final concentration of 0.5% (w/v) sarcosyl with gentle agitation for 30 minutes at room temperature. The samples were centrifuged at 14,000 rpm for five minutes, and the supernatants containing, PrPc (uninfected) and a mixture of PrPc and PrPsc (infected), were collected. PrPsc is over represented in scrapie-infected hamster brain tissue relative to PrPc. Five milliliters of brain material for analysis was prepared by combining 1 ml of normal hamster 10% brain homogenate in 0.5% sarcosyl with 0.33 ml of scrapie-infected brain material and 3.67 ml of TBS buffer (Pierce, Rockford, Ill.) containing 1% of casein and 1% of BSA (Sigma, St. Louis, Mo.). The final ratio of normal to scrapie-infected brain homogenate was 3:1 which gave very approximately equivalent amounts of PrPc and PrPsc. This material was contacted with the trimer bead library and processed according to the procedures. Following washing, the beads were variously treated. In one method, they were incubated with PK to digest PrPc bound to the beads, in another, they were stained for the presence of PrPc. This was accomplished by incubation of the beads with 3F4 antibody, washing, then adding phosphatase conjugated secondary antibody specific for 3F4, washing and adding a phosphatase substrate, to visualize beads binding PrPc, 3F4, secondary antibody or phosphatase. Thus, those beads that bound PrPc were red. Once embedded in the gel a second chemiluminescent substrate specific for phosphatase was added, in some experiments, to produce a light signal from the red beads. PrPc, PrPsc and PrPres were transferred from the agarose as described above in the presence of 6 M guanidinium/HCl, which also caused the denaturation of the prion protein. Denaturation and immobilization of PrPsc on the capture membrane facilitated the immunodetection of PrPsc, as well as PrPc. Upon alignment of these spots with the previously stained beads, different populations of beads are possible. Those beads that directly bound detection reagents such as 3F4 and those that bound PrPc plus PrPsc, or PrPc alone would be stained red. Those beads that bound only or preferentially PrPsc would produce a signal on the membrane, but should not be stained red. These were selected as PrPsc specific beads though they were further tested as beads that might theoretically bind both PrPc and/or PrPsc at a site on the prion protein that prevented binding of 3F4. In FIG. 1, beads from the trimer library that did not produced the signal at the first chemiluminescent detection (before denaturing step), but produced the signal at the second chemiluminescent detection (after denaturing step), and therefore, were candidates for sequencing, were assigned with numbers.

Various versions of the methodology described in this Example are given in the Tables set forth herein.

For example, in Tables 10A and B, below, screening of 6-mer libraries (100-300 μm and 65 μm) was performed in presence of sporadic CJD brain material spiked into normal human plasma. Beads were exposed to 0.5% brain homogenate spiked into normal human plasma collected into CPD, and then were treated with PK 100 μg/ml. To confirm that PK does not fully digest peptides from the beads, the resins were treated with 1% (w/v) casein and 5% (w/v) human serum albumin and 100 μg/ml of PK prior to sequencing.

TABLE 10A

Six-amino acid sequences that bind to huPrPc, huPrPsc or both

| SEQ IN NO | Screened material | Sequence | Bead color | Light production after denaturation |
|---|---|---|---|---|
| 154 | huPrPsc no PK* | RES(na)NVA | White | Strong |
| 155 | * | ES(na)PRQA | White | Strong |
| 156 | * | VARENIA | White | Strong |
| 157 | * | RWEREDA | Pink | Strong |
| 158 | HuPrPsc no PK** | EWWETV | White | Medium |
| 159 | ** | SVYQLDA | White | Medium |
| 160 | ** | (na)HEFYGA | White | Medium |
| 161 | ** | HE(na)(na)LVA | White | Medium |
| 162 | ** | A(na)VPV(na)A | Pink | Medium |
| 163 | ** | YFDYWLA | Pink | Medium |
| 164 | ** | FE(na)HRQA | Pink | Medium |
| 165 | ** | WRHEPAA | Red | Medium |
| 166 | huPrPsc + PK*** | SS(na)KKDA | White | Medium |
| 167 | *** | R(na)DKEAA | White | Medium |
| 168 | huPrPsc + PK**** | (na)HEIFPA | NA | Medium |
| 169 | **** | KWYHHRA | NA | Medium |
| 170 | **** | HWWPHNA | NA | Medium |
| 171 | **** | HWQVFYA | NA | Medium |
| 172 | **** | FHE(na)EIA | NA | Medium |
| 173 | **** | HADF(na)QA | NA | Medium |

*0.5% sporadic CJD brain homogenate (huPrPsc) without PK treatment
**5% huPrPsc without PK treatment
***0.5% huPrPsc with PK treatment, but no color development
****5% huPrPsc with PK treatment, but with no color development
"NA" indicates that it was not done, na indicates naphthyl-alanine

TABLE 10B

Six-amino acid sequences that bind to huPrPsc

| SEQ ID NO | Screened material | Sequence | Bead color | Light signal after denaturation |
|---|---|---|---|---|
| 174 | HuPrPsc + PK* | ALHFETA | White | Weak |
| 175 | * | DDPTGFA | White | Weak |
| 176 | * | VAPGLGA | White | |
| 177 | * | IFRLIEA | White | Weak |
| 178 | * | GLERPEA | White | Weak |
| 179 | * | IVVRLWA | Pink | Weak |

TABLE 10B-continued

Six-amino acid sequences that bind to huPrPsc

| SEQ ID NO | Screened material | Sequence | Bead color | Light signal after denaturation |
|---|---|---|---|---|
| 180 | * | WHNPHYA | Pink | Weak |
| 181 | * | LIYKSDA | Pink | Weak |
| 182 | huPrPsc no PK** | EKPIFNA | White | Weak |
| 183 | ** | HWSEPAA | Red | Weak |
| 184 | ** | GHNWKEA | Pink | Strong |
| 185 | ** | YWHHDDA | Pink | Strong |
| 186 | ** | GYPKENA | Pink | Strong |
| 187 | ** | PVYWLYA | White | Strong |
| 188 | huPrPsc no PK*** | FGEHTPA | White | Weak |
| 189 | *** | FQGTREA | White | Strong |
| 190 | *** | TGTNRYA | White | Strong |
| 191 | *** | KWATRYA | White | Strong |
| 192 | *** | NSTKFDA | White | Strong |
| 193 | *** | LIYKEEA | Pink | Strong |
| 194 | *** | EHATYRA | White | Strong |
| 215 (Control) | **** | DRDLTFA | White | None |
| 216 (Control) | **** | HNWWIIA | White | None |
| 217 (Control) | **** | EVKIGNA | White | None |

*100-300 µm beads screened with sporadic CJD brain homogenate (huPrPsc) with PK treatment
**100-300 µm beads screened with huPrPsc without PK treatment
***65 µm beads screened with huPrPsc without PK treatment
****control beads demonstrate lack of significant digestion of the ligand following incubation with PK in the absence of PrP.

In Table 10C, below, screening of 3-mer library was performed in the presence of brain homogenate prepared from a patient with sporadic CJD (huPrPsc) and beads were treated with PK before the immunodetection of PrP specific binders. In this assay, 10 mg of resin per column was incubated with 1 ml of 0.5% (w/v) or 1% (w/v) brain homogenate diluted into CPD and containing 0.05% or 0.1% (v/v) sarcosyl, respectively, and 0.2 mM of the protease inhibitor (PMSF). Appropriate washes described in the general protocol were performed, and beads were treated with 1 ml of PK (100 μg/ml) at 37° C. for one hour. Then followed the general procedures described above. Sequences obtained in two experiments are listed in Table 1° C. The appropriate concentration of brain homogenate material present during the incubation is indicated for each group of sequences.

In Table 10D, resin from a combinatorial library in the amount of 5 mg of dry weight per column was incubated with 1 ml of 0.1% (w/v) brain homogenate diluted into PBS or CPD and containing 0.01% (v/v) sarcosyl and 0.2 mM of PMSF. All the procedures were performed according to above mentioned protocols.

TABLE 10C

| Three-amino acid sequences that bind to huPrPc, huPrPsc, or both | | | | |
|---|---|---|---|---|
| SEQ ID NO | Material screened | Sequence | Bead color | Light signal after denaturation |
| 195 | huPrPsc + PK* | HND | White | Medium |
| 196 | * | HER | Red | Medium |
| 197 | * | HGD | Red | Strong |
| 198 | * | HSD | Red | Strong |
| 199 | * | HFD | Red | Strong |
| 200 | **** | WND | Red | None |
| 201 | **** | YEH | Red | None |
| 202 | **** | HWD | Red | None |
| 203 | **** | YHD | Red | None |
| 204 | **** | YDW | Red | None |
| 205 | **** | WDY | Red | None |

TABLE 10C-continued

| Three-amino acid sequences that bind to huPrPc, huPrPsc, or both | | | | |
|---|---|---|---|---|
| SEQ ID NO | Material screened | Sequence | Bead color | Light signal after denaturation |
| 218 (Control) | ***** | SIV | White | None |
| 219 (Control) | ***** | AYP | White | None |
| 206 | huPrPsc no PK** | HYD (3x) | Red | Strong |
| 207 | ** | HWD | Red | Strong |
| 208 | ** | WTD | Red | Strong |
| 209 | huPrPsc + PK*** | FPK | White | Medium |
| 210 | *** | HWK | White | Medium |
| 211 | *** | WEE | White | Medium |
| 212 | *** | LLR | White | Medium |

*0.5% huPrPsc in 0.05% Sarcosyl plus PK treatment
**1.0% huPrPsc in 0.1% Sarcosyl without PK treatment
***1.0% huPrPsc in 0.1% Sarcosyl with PK treatment
****beads were selected from the gel before transfer
*****beads were taken following washing
3 x denotes sequences detected three times

TABLE 10D

| Three-amino acid sequences that bind to huPrPc, huPrPsc, or both | | | | |
|---|---|---|---|---|
| SEQ ID NO | Material screened | Sequence | Bead color | Light signal after denaturation |
| 147 | huPrPsc in CPD* | WEH | Red | Strong |
| 152 | * | YDY | Red | Strong |
| 206 | * | HYD | Red | Strong |
| 213 | huPrPsc in PBS** | SYF | White | Weak |
| 214 | ** | EYY | Red | Strong |

Example 2

Secondary Screening of Ligands

The following examples provide-information on secondary screening of ligands selected from the various libraries during the primary screening to further confirm that the ligands bind PrP.

Binding of PrPc from normal human brain to trimer resins is shown in FIGS. 2A-B. Ten mg of each resin (Amino, HYD (SEQ ID NO:206)), RWD (SEQ ID NO:113), SYA (SEQ ID NO:108), SYF (SEQ ID NO:213), and YEY (SEQ ID NO:154)), per column was used. The amino resin is the base polymer from which the peptides are synthesized and has some affinity to prion protein. Resins were equilibrated with either PBS, or CPD at pH 7.4. Frozen normal human brain tissue was used as the source of huPrPc. It was first thawed on wet ice. A sample of 10% brain homogenate prepared in PBS or in CPD was solubilized with 1% Sarcosyl and clarified by centrifugation at 14,000 rpm for five minutes. The supenatant was recovered and diluted 100 times to a final concentration of brain homogenate and Sarcosyl of 0.1% and 0.01%, respectively. One milliliter of this material was applied to the column and the flow through was collected. Beads were washed with 20 ml of PBS or CPD, and 1 mg of beads (dry weight) was used for evaluation of PrPc binding by Western blot as described below.

After washing, approximately 1 mg dry weight equivalent of beads was suspended in 100 ul of buffer, and was heated at 100° C. for 10 minutes in 30 μl of Laemmli buffer containing 2% β-mercaptoethanol. The beads were centrifuged at 14,000 rpm for one minute, and the supernatant was evaluated by Western blotting and probing for PrP. Samples were resolved on NuPAGE 12% Bis-Tris gel (Invitrogen Life Technologies, Carlsbad, Calif., USA) under reduced denaturing conditions, and electroblotted to nitrocellulose membrane (Invitrogen Life Technologies, Carlsbad, Calif., USA). Specific PrP bands were visualized using monoclonal antibody 3F4 diluted 1:10,000. The blots were developed using SuperSignal West Pico detection system (Pierce, Rockford, Ill., USA) containing chemiluminescent reagent for horseradish peroxidase detection. Signals were recorded on X-Omat™ Blue XB-1 film (Eastman Kodak Company, Rochester, N.Y., (SEW ID NO:113), SYA (SEQ ID NO:108), WEY (SEQ ID NO:102), WSD (SEQ ID NO:115), YID (SEQ ID NO:112), YFE (SEQ ID NO:106), YEY (SEQ ID NO:154), and WQD) per column was used and processed according to the general protocol described above. Columns were equilibrated with PBS, pH 7.4 Frozen brain tissue from a sporadic CJD patient was used for the PrPsc preparation. It also contained PrPc. Sample of 10% brain homogenate was prepared in PBS treated with 1% sarcosyl and clarified by centrifugation at 14,000 rpm for five minutes. The supernatant was recovered and diluted 100 times to give a final concentration of brain homogenate and Sarcosyl of 0.1% and 0.01%, respectively. One milliliter of this material was applied to the beads and incubated at room temperature in a batch format for three hours. The beads were then washed with 20 ml of PBS, and 1 mg of beads (dry weight) was incubated with PBS or with PK (100 μg/ml) in PBS at 37° C. for one hour. These conditions fully digested PrPc. Thus, this helped to discriminate between PrPsc and PrPc specific-ligands. The usual processing of the beads for Western blot followed as described in Example 1.

Figure 4A:
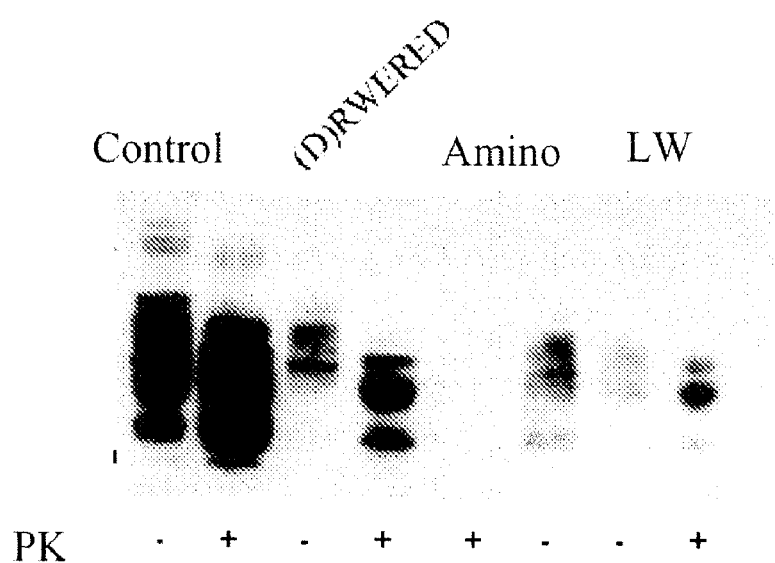
FIGS. 4A-B Binding of huPrPsc from extracts of CJD infected human brain to affinity resins in a column format. Peptide sequences are indicated at the top of the gel. Samples previously digested with PK are identified as + and undigested as Controls included 20 µl of 1% brain homogenate. PrPc and PrPsc were specifically detected using monoclonal antibody 3F4 and visualized by detection of a chemiluminescent signal.
Figure 4B:
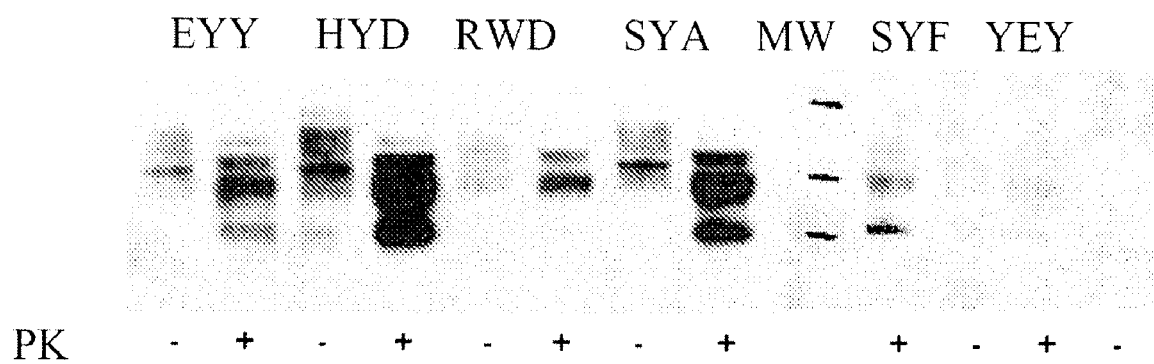
Figure 5:
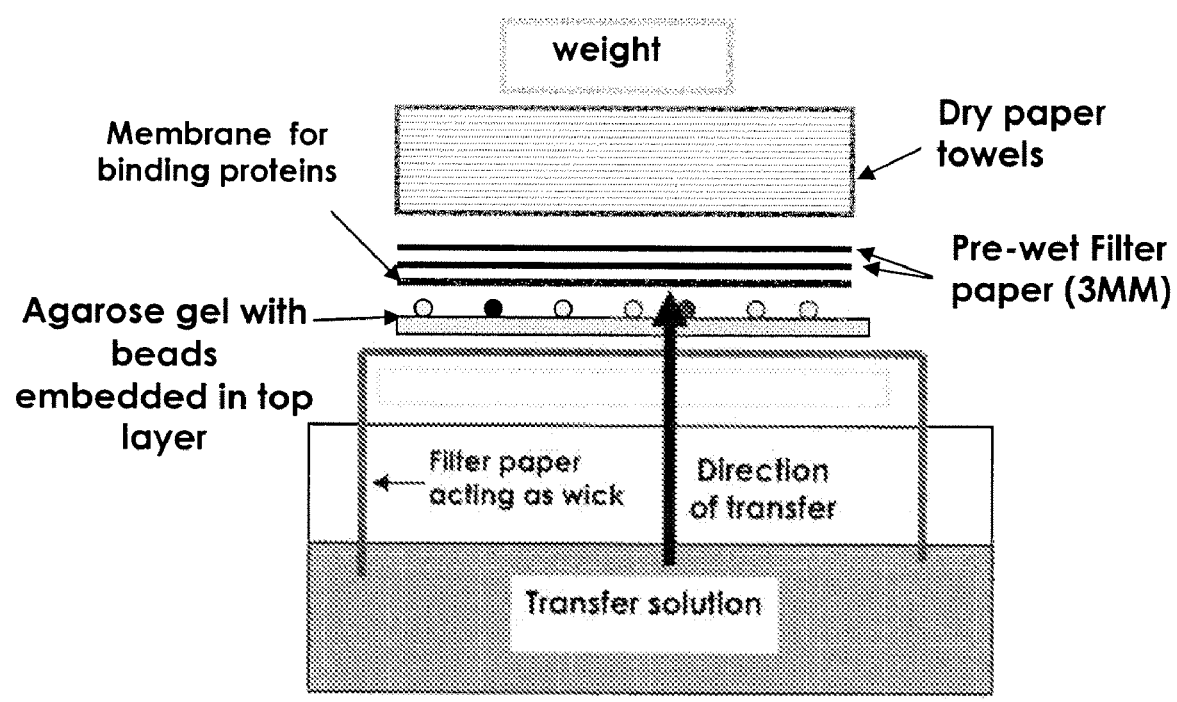
FIG. 5 Diagram of the "bead blot" transfer set-up. Beads are arrayed in a gel following incubation with starting materials. Bound protein is transferred from the beads and captured on the membrane via capillary transfer of buffer as indicated.

Binding of PrPsc in a brain homogenate taken from a sporadic CJD patient to resins in a flow-through format is shown in FIGS. 4A-B. Fifty milligrams of each resin (Amino, RWERED (SEQ ID NO:157), LW (SEQ ID NO:50), EYY (SEQ ID NO:214), HYD (SEQ ID NO:206)), RWD (SEQ ID NO:113), SYA (SEQ ID NO:108), SYF (SEQ ID NO:213), and YEY (SEQ ID NO:154)) was used in experiment. The Captiva 96-well Filter Plate (CaptiVac Vacuum Sistem, ANSYS Technologies, Inc, Cat.#796) was used instead of individual columns. Resins were prepared according to the general protocol described above. Resins were equilibrated with CPD at pH 7.4. Frozen brain tissue from a sporadic CJD patient was used as the source of huPrPc and huPrPsc. A sample of 10% brain homogenate was prepared in CPD treated with 1% sarcosyl and clarified by centrifugation at 14,000 rpm for five minutes. The supernatant was recovered and diluted ten times to give a final concentration of brain homogenate and sarcosyl of 1% and 0.1% respectively. To each well, 250 μl of this material was applied. The material was allowed to pass through the resin under gravity with a contact time of about four minutes and flow through was collected. Resins were washed with 2.5 ml of CPD. One milligram of beads (dry weight) was incubated with PK (100 μg/ml) at 37° C. for one hour. The usual processing of the beads for Western blot followed, as described above.

Although methods and materials similar or equivalent to those described herein can be used in the practice or testing of the present invention, suitable methods and material are described above. All publications, patent applications, patents and other cited references mentioned herein are incorporated by reference in their entirety. In addition, the materials, methods, and examples are illustrative only and not intended to be limiting.

The foregoing description is provided for describing various embodiments relating to the invention. Various modifications, additions and deletions may be made to these embodiments and/or structures without departing from the scope and spirit of the invention.

Example 3

Visualization of PrPc Bound to Resins

To visualize the binding of PrPc to affinity resins, normal brain homogenate was bound to amino DVR (SEQ ID NO:114) resin in a column format, and the location of the protein in the interior and at the exterior of the beads was visualized by a chromogenic substrate. A 0.5 ml column of affinity ligand DVR (SEQ ID NO:114), which was synthesized on Toyopearl 650-M amino resin, was packed into a PIKSI column (ProMetic BioSciences Ltd, Montreal, Québec, Canada). To the column was applied 1.5 ml of 1% normal hamster brain homogenate (HaBH) diluted in a working buffer (WB) (20 mM citrate, 140 mM NaCl, pH 7.0) at a flow rate of 0.5 ml/min, which was controlled by a peristaltic pump. Following loading of HaBH, the columns were washed with 5 ml of WB. The beads were removed from the column, chopped with a razor blade to expose the interior of the beads, and incubated with primary antibody 3F4 diluted 1:4000 in 1% casein buffer (Pierce, Rockford, Ill.) for 1 hr at room temperature with agitation through rotating. The beads were washed with TBS, pH 7.4 (Invitrogen Life Technologies, Carlsbad, Calif., USA) and incubated for 1 hr at room temperature with rotation with an alkaline-phosphatase labeled secondary goat anti-mouse antibody (KPL, Gaithersburg, Md.) diluted 1:1000 in 1% casein. The beads were washed with 10 ml TBS at pH 7.4, followed by 5 ml TBS at pH 9.5. The beads were incubated with BCIP/NBT alkaline phosphatase substrate (Sigma-Aldrich, St. Louis, Mo.) for several hours and observed under a stereomicroscope. The exterior surface of the beads was stained brown/blue, but the interior surface remained white, indicating that the protein bound to the exterior of the beads.

Example 4

Removal of PrPsc from Red Blood Cell Concentrates

Red Blood Cell Concentrates (RBCCs) were spiked with brain homogenate from hamsters infected with Scrapie at concentrations orders of magnitude higher than that likely to be found endogenously in the blood of infected animals. The spiked RBCCs were passed in succession through columns of resins with various affinity ligands in order to evaluate the ability of the affinity ligands to bind and remove PrP, when present at high concentration, from RBCCs.

Ten units of type O negative red blood cell concentrates (RBCCs) were leukoreduced on Pall Leukotrap filters (Pall, East Hills, N.Y.), pooled, and spiked with 0.1% scrapie hamster brain homogenate in 0.1% sarkosyl. The spike was added at 2 ml/min, with agitation. The spiked RBCCs were subdivided into 10 equal portions of 300 ml each into transfer bags (Fenwal Products, Baxter Healthcare Corporation, Deerfild, Ill.).

Five columns, each containing 10 ml of a specific resin, were set up in series, so that the flow through of column one, containing unbound material was applied to column two. This was continued until all 5 columns were exposed to RBCCs. Through column one, 300 ml of spiked RBCCs was passed, the flow through collected, and run over column two, and so on, until all of the columns were exposed to RBCCs. The beads in the column were collected, and 100 μl sample of beads was washed, and divided into two portions. One portion was incubated with Proteinase K (in Table 11, sample incubated with Proteinase K is denoted +PK, sample not incubated with Proteinase K is denoted −PK) at 1 mg/ml for 1 hr at 37° C. The proteins that bound to both the +PK and −PK beads were eluted from the beads by boiling in 2× sample buffer (NuPAGE, Helixx Technologies Inc., Toronto, Ontario, Canada). Each sample in the amount of 10 μl of was loaded on a 12% Bis-Tris SDS-PAGE gel (Invitrogen) and electrophoresed for 45 min. The proteins from the gel were transferred to a membrane and the PrP protein was detected in a Western blot using mouse anti-human PrP antibody 3F4 as the primary antibody, goat anti-mouse alkaline phosphatase conjugated antibody as the secondary antibody, and detected with Western Breeze chemiluminescent detection (Invitrogen). The bands on the gel, obtained by eluting resin-bound protein, indicate the presence of PrPres on the beads that were derived from the flow-through of the previous column (or starting material in the case of column 1).

PrPres was found on beads from columns 1-5 for the negative control, acetylated SYA (Ac-SYA) (SEQ ID NO:108) resin, indicating that this resin did not bind PrPsc. PrPres was found in high amounts on column 1, and in decreased amounts on column 2 for DVR (SEQ ID NO:114) and SYA (SEQ ID NO:10), with only a small amount of PrPres present on beads from column 3. This indicated that these resins remove all of the PrPres to the limit of detection of the Western blot in 3 columns, or 30 ml of resin. Resins YVHEA (SEQ ID NO:63) and (D)ES(na)PRQ-EACA (SEQ ID NO:226-EACA) also show decreasing amounts of PrPres on columns 1 through 3; however, there is more PrPres bound to column 3 than in the previous two resins. An equivalent amount of PrPres is found on every column of WFVEA (SEQ ID NO:225), indicating that this resin binds a small amount of PrPres on every column, but does not bind and remove all of the prion protein to the limit of detection. As the spike was several fold higher than the amount of PrP that has been observed endogenously in the blood of animals, these results indicated that certain of these resins had the ability to remove most, if not all of the endogenous PrPres present in blood.

TABLE 11

Gel loading pattern for electrophoresis of samples in Example 4.

| Resins SYA & Ac-SYA (SEQ ID NO: 10) | Resins DVR (SEQ ID NO: 114), YVHEA (SEQ ID NO: 63), (D)ES(na)PRQ (SEQ ID NO: 226), WFDEA (SEQ ID NO: 225) |
|---|---|
| 1. MWM | 1. MWM |
| 2. Column #1 − PK | 2. Column #1 − PK |
| 3. Column #1 + PK | 3. Column #1 + PK |
| 4. Column #2 − PK | 4. Column #2 − PK |
| 5. Column #2 + PK | 5. Column #2 + PK |
| 6. Column #3 − PK | 6. Column #3 − PK |
| 7. Column #3 + PK | 7. Column #3 + PK |
| 8. Column #4 − PK | 8. Column #4 − PK |
| 9. Column #4 + PK | 9. Column #4 + PK |
| 10. Scrapie brain homogenate − PK (1:100) | 10. Column #5 − PK |
| 11. Scrapie brain homogenate − PK (1:10) | 11. Column #5 + PK |
| 12. Scrapie brain homogenate − PK (1:2) | 12. Scrapie brain homogenate − PK (1:100) |
| 13. Scrapie brain test material − PK | 13. Scrapie brain homogenate − PK (1:10) |
| 14. Scrapie brain test material + PK | 14. Scrapie brain homogenate − PK (1:2) |
| 15. MWM | 15. Scrapie brain test material − PK |
| | 16. Scrapie brain test material + PK |
| | 17. MWM |

MWM denotes molecular weight markers

What is claimed is:

1. An isolated prion-binding peptide ligand, wherein the ligand is capable of binding to a peptide having the amino acid sequence RYPGQ (SEQ ID NO:1); and wherein the ligand is a peptide consisting of an amino acid sequence selected from the group consisting of SEQ ID NOS:5-13.

2. The ligand of claim 1, wherein the ligand has a molecular weight of less than approximately 6 kDa.

3. An isolated prion-binding ligand, wherein the ligand is capable of binding to a native form of prion protein (PrPc) and is a peptide consisting of an amino acid sequence SEQ ID NO: 116.

4. The ligand of claim 3, wherein the ligand is capable of binding to a native prion protein that infects humans (huPrPc).

5. A method of detecting a prion protein in a sample, comprising:
contacting the sample with a ligand according to claim 1 under conditions sufficient to cause formation of a complex between the prion protein and the ligand; and
detecting the complex in the sample.

6. The method of claim 5 wherein the sample is a biological sample.

7. The method of claim 6 wherein the biological sample is selected from the group consisting of whole blood, white cells, mononuclear cells, platelet concentrates, blood, plasma, serum, cerebrospinal fluid, urine, saliva, milk, ductal fluid, tears, semen, feces, tonsils, lymph nodes, collagen, brain extracts and gland extracts.

8. The method of claim 6 wherein the ligand is attached to a solid support prior to contacting the sample.

9. The method of claim 8 wherein the solid support is selected from the group consisting of membranes and resins.

10. The method of claim 8 wherein the solid support is a resin selected from the group consisting of polymethacrylate, agarose, sepharose, cross-linked agarose, composite cross-linked polysaccharides, celite, polyvinyl D, fluoride acrylate, polystyrene and cellulose.

11. The method of claim 8 wherein the solid support is polymethacrylate resin.

12. The method of claim 8 wherein the solid support is a membrane selected from the group consisting of nylon and cellulose.

13. A method of removing a prion protein from a sample, comprising:
contacting the sample with a ligand according to claim 1 capable of binding to one or more peptides or polypeptides derived from a prion protein selected from the group consisting of PrPc, PrPsc and PrPr, under conditions sufficient to cause formation of a complex between the prion protein and the ligand; and
removing the complex from the sample.

14. The method of claim 13 wherein the sample is a biological sample.

15. The method of claim 13 wherein the biological sample is selected from the group consisting of whole blood, white cells, mononuclear cells, platelet concentrates, blood, plasma, serum, cerebrospinal fluid, urine, saliva, milk, ductal fluid, tears, semen, feces, tonsils, lymph nodes, collagen, brain extracts and gland extracts.

16. The method of claim 13 wherein the ligand is attached to a solid support prior to contacting the sample.

17. The method of claim 13 wherein the solid support is selected from the group consisting of membranes and resins.

18. The method of claim 13 wherein the solid support is a resin selected from the group consisting of polymethacrylate, agarose, sepharose, cross-linked agarose, composite cross-linked polysaccharides, celite, polyvinyl D, fluoride acrylate, polystyrene and cellulose.

19. The method of claim 13 wherein the solid support is polymethacrylate resin.

20. The method of claim 13 wherein the solid support is a membrane selected from the group consisting of nylon and cellulose.

21. A composition for binding prion proteins, comprising:
    a ligand according to claim 1; and
    a solid support, wherein the ligand is attached to the solid support.

22. The composition of claim 21 wherein the solid support is selected from the group consisting of membranes and resins.

23. A method of detecting a prion protein in a sample, comprising:
    contacting the sample with a ligand according to claim 3 capable of binding to a native form of a prion protein under conditions sufficient to cause formation of a complex between the prion protein and the ligand; and
    detecting the complex in the sample.

24. A method of removing a prion protein from a sample, comprising:
    contacting the sample with a ligand according to claim 3 capable of binding to a native form of a prion protein under conditions sufficient to cause formation of a complex between the prion protein and the ligand; and
    removing the complex from the sample.

25. A composition for binding prion proteins, comprising:
    a ligand according to claim 3; and
    a solid support, wherein the ligand is attached to the solid support.

26. A method of detecting a prion protein in a sample, comprising:
    contacting the sample with a ligand according to claim 1 capable of binding to a native form of a prion protein under conditions sufficient to cause formation of a complex between the prion protein and the ligand; and
    detecting the complex in the sample.

27. A method of removing a prion protein from a sample, comprising:
    contacting the sample with a ligand according to claim 1 capable of binding to a native form of a prion protein under conditions sufficient to cause formation of a complex between the prion protein and the ligand; and
    removing the complex from the sample.

* * * * *